(12) United States Patent
Dorn

(10) Patent No.: US 8,652,193 B2
(45) Date of Patent: Feb. 18, 2014

(54) IMPLANT DELIVERY DEVICE

(75) Inventor: Jurgen Dorn, Neulussheim (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 1434 days.

(21) Appl. No.: 11/914,094

(22) PCT Filed: May 5, 2006

(86) PCT No.: PCT/IB2006/002582
§ 371 (c)(1),
(2), (4) Date: May 15, 2008

(87) PCT Pub. No.: WO2007/004076
PCT Pub. Date: Jan. 11, 2007

(65) Prior Publication Data
US 2008/0234796 A1    Sep. 25, 2008

Related U.S. Application Data

(60) Provisional application No. 60/679,025, filed on May 9, 2005.

(51) Int. Cl.
*A61F 2/06* (2013.01)
(52) U.S. Cl.
USPC .......................................... 623/1.11; 606/151
(58) Field of Classification Search
USPC .................................. 606/151, 191; 623/1.11
See application file for complete search history.

(56) References Cited

U.S. PATENT DOCUMENTS

| 606,557 A | 6/1898 | Kelso et al. |
| 3,352,306 A * | 11/1967 | Hrisch ..................... 604/164.01 |
| 3,467,101 A | 9/1969 | Fogarty et al. |
| 3,485,234 A | 12/1969 | Stevens |

(Continued)

FOREIGN PATENT DOCUMENTS

| AU | 654075 | 8/1993 |
| CA | 2391420 A1 | 5/2001 |

(Continued)

OTHER PUBLICATIONS

Kolobow, Theodor et al, A Thin-Walled Nonkinking Catheter for Peripheral Vascular Cannulation, vol. 68, No. 4, Surgery, pp. 625-629, Oct. 1970.

(Continued)

*Primary Examiner* — Gregory Anderson
(74) *Attorney, Agent, or Firm* — Rutan & Tucker, LLP

(57) ABSTRACT

An implant delivery device preferably includes a first shaft having a proximal portion and a distal portion. The first shaft includes an outer surface and an inner surface defining a first lumen along a longitudinal axis. The distal portion includes a tip defining a taper in the distal direction toward the longitudinal axis and terminating at a distal opening. The device also includes a second shaft having a proximal portion and a distal portion and an inner surface defining a second lumen therebetween having a first cross-section. The second shaft is disposed within the first lumen such that the second lumen is generally coaxial with the first lumen to define a chamber. The distal portion of the second shaft terminates in a port having an opening in communication with the distal opening of the first shaft. The port preferably includes a second cross-section greater than the first cross-section.

58 Claims, 15 Drawing Sheets

(56) References Cited

U.S. PATENT DOCUMENTS

| | | |
|---|---|---|
| 3,585,707 A | 6/1971 | Stevens |
| 3,841,308 A | 10/1974 | Tate |
| 4,351,341 A | 9/1982 | Goldberg et al. |
| 4,498,691 A | 2/1985 | Cooke |
| 4,516,972 A * | 5/1985 | Samson ............ 604/526 |
| 4,563,181 A | 1/1986 | Wijayarathna et al. |
| 4,576,608 A | 3/1986 | Homsy |
| 4,580,568 A | 4/1986 | Gianturco |
| 4,614,188 A | 9/1986 | Bazell et al. |
| 4,636,346 A | 1/1987 | Gold et al. |
| 4,665,604 A | 5/1987 | Dubowik |
| 4,665,906 A | 5/1987 | Jervis |
| 4,665,918 A | 5/1987 | Garza |
| 4,759,748 A | 7/1988 | Reed |
| 4,817,613 A | 4/1989 | Jaraczewski et al. |
| 4,842,590 A | 6/1989 | Tanabe et al. |
| 4,863,442 A | 9/1989 | DeMello et al. |
| 4,898,591 A | 2/1990 | Jang |
| 4,921,484 A | 5/1990 | Hillstead |
| 5,019,057 A | 5/1991 | Truckai |
| 5,026,377 A | 6/1991 | Burton et al. |
| 5,037,404 A | 8/1991 | Gold et al. |
| 5,057,092 A | 10/1991 | Webster, Jr. |
| 5,061,257 A | 10/1991 | Martinez et al. |
| 5,067,959 A | 11/1991 | Korthoff |
| 5,078,702 A | 1/1992 | Pomeranz |
| 5,089,006 A | 2/1992 | Stiles |
| 5,160,341 A | 11/1992 | Brenneman et al. |
| 5,176,660 A | 1/1993 | Truckai |
| 5,190,058 A | 3/1993 | Jones et al. |
| 5,190,546 A | 3/1993 | Jervis |
| 5,201,757 A | 4/1993 | Heyn et al. |
| 5,201,901 A | 4/1993 | Harada et al. |
| 5,221,270 A | 6/1993 | Parker |
| 5,234,407 A * | 8/1993 | Teirstein et al. ............ 604/528 |
| 5,234,416 A | 8/1993 | Macaulay et al. |
| 5,242,399 A * | 9/1993 | Lau et al. .............. 604/104 |
| 5,254,107 A | 10/1993 | Soltesz |
| 5,275,152 A | 1/1994 | Krauter et al. |
| 5,282,824 A | 2/1994 | Gianturco |
| 5,290,295 A | 3/1994 | Querals et al. |
| 5,334,169 A | 8/1994 | Brown et al. |
| 5,338,295 A | 8/1994 | Cornelius et al. |
| 5,346,498 A | 9/1994 | Greelis et al. |
| 5,389,100 A | 2/1995 | Bacich et al. |
| 5,391,172 A | 2/1995 | Williams et al. |
| 5,403,292 A | 4/1995 | Ju |
| 5,405,338 A | 4/1995 | Kranys |
| 5,405,380 A | 4/1995 | Gianotti et al. |
| 5,409,478 A | 4/1995 | Gerry et al. |
| 5,415,664 A | 5/1995 | Pinchuk |
| 5,433,723 A | 7/1995 | Lindenberg et al. |
| 5,443,477 A | 8/1995 | Marin et al. |
| 5,453,090 A | 9/1995 | Martinez et al. |
| 5,454,795 A | 10/1995 | Samson |
| 5,458,615 A * | 10/1995 | Klemm et al. ............ 606/198 |
| 5,464,408 A | 11/1995 | Duc |
| 5,476,608 A | 12/1995 | Boyer et al. |
| 5,484,444 A | 1/1996 | Braunschweiler et al. |
| 5,507,768 A | 4/1996 | Lau et al. |
| 5,522,883 A | 6/1996 | Slater et al. |
| 5,540,712 A | 7/1996 | Kleshinski et al. |
| 5,545,151 A | 8/1996 | O'Connor et al. |
| 5,556,426 A | 9/1996 | Popadiuk et al. |
| 5,569,197 A | 10/1996 | Helmus et al. |
| 5,569,218 A | 10/1996 | Berg |
| 5,571,114 A | 11/1996 | Devanaboyina |
| 5,571,135 A | 11/1996 | Fraser et al. |
| 5,571,168 A | 11/1996 | Toro |
| 5,591,172 A | 1/1997 | Bachmann et al. |
| 5,591,195 A | 1/1997 | Taheri et al. |
| 5,597,378 A | 1/1997 | Jervis |
| 5,601,568 A | 2/1997 | Chevillon et al. |
| 5,601,591 A | 2/1997 | Edwards et al. |
| 5,603,698 A | 2/1997 | Roberts et al. |
| 5,603,705 A | 2/1997 | Berg |
| 5,607,422 A | 3/1997 | Smeets et al. |
| 5,607,442 A | 3/1997 | Fischell et al. |
| 5,618,300 A | 4/1997 | Marin et al. |
| 5,630,806 A | 5/1997 | Inagaki et al. |
| 5,643,278 A | 7/1997 | Wijay |
| 5,643,339 A | 7/1997 | Kavteladze et al. |
| 5,645,559 A | 7/1997 | Hachtman et al. |
| 5,658,263 A | 8/1997 | Dang et al. |
| 5,658,264 A | 8/1997 | Samson |
| 5,662,622 A | 9/1997 | Gore et al. |
| 5,662,703 A | 9/1997 | Yurek |
| 5,667,523 A | 9/1997 | Bynon et al. |
| 5,674,208 A | 10/1997 | Berg |
| 5,683,451 A | 11/1997 | Lenker et al. |
| 5,690,644 A | 11/1997 | Yurek et al. |
| 5,690,645 A | 11/1997 | Van Erp |
| 5,695,483 A | 12/1997 | Samson |
| 5,695,499 A | 12/1997 | Helgerson et al. |
| 5,697,948 A | 12/1997 | Marin et al. |
| 5,700,269 A | 12/1997 | Pinchuk et al. |
| 5,702,373 A | 12/1997 | Samson |
| 5,702,418 A | 12/1997 | Ravenscroft |
| 5,707,376 A | 1/1998 | Kavteladze et al. |
| 5,707,386 A | 1/1998 | Schnepp-Pesch |
| 5,709,702 A | 1/1998 | Cogita |
| 5,709,703 A | 1/1998 | Lukic et al. |
| 5,711,909 A | 1/1998 | Gore et al. |
| 5,713,851 A | 2/1998 | Boudewijn et al. |
| 5,713,917 A | 2/1998 | Leonhardt et al. |
| 5,716,393 A | 2/1998 | Lindenberg |
| 5,722,669 A | 3/1998 | Shimizu et al. |
| 5,725,513 A | 3/1998 | Ju et al. |
| 5,725,570 A | 3/1998 | Heath |
| 5,725,571 A | 3/1998 | Imbert et al. |
| 5,725,572 A | 3/1998 | Lam et al. |
| 5,733,267 A | 3/1998 | Del Toro |
| 5,733,400 A | 3/1998 | Gore et al. |
| 5,735,859 A | 4/1998 | Fischell |
| 5,735,892 A | 4/1998 | Myers et al. |
| 5,741,270 A | 4/1998 | Hansen et al. |
| 5,741,327 A | 4/1998 | Frantzen |
| 5,743,874 A | 4/1998 | Fischell |
| 5,749,880 A | 5/1998 | Banas et al. |
| 5,749,918 A | 5/1998 | Hogendijk et al. |
| 5,749,921 A | 5/1998 | Lenker et al. |
| 5,755,686 A | 5/1998 | O'Neill et al. |
| 5,759,186 A | 6/1998 | Bachmann et al. |
| 5,766,184 A | 6/1998 | Matsuno et al. |
| 5,772,668 A | 6/1998 | Summers et al. |
| 5,772,669 A | 6/1998 | Vrba |
| 5,782,811 A | 7/1998 | Samson et al. |
| 5,782,855 A | 7/1998 | Lau |
| 5,782,904 A | 7/1998 | White et al. |
| 5,788,626 A | 8/1998 | Thompson |
| 5,788,707 A | 8/1998 | Del Toro et al. |
| 5,792,124 A | 8/1998 | Horrigan et al. |
| 5,817,101 A | 10/1998 | Fiedler |
| 5,817,102 A | 10/1998 | Johnson et al. |
| 5,820,612 A | 10/1998 | Berg |
| 5,824,037 A | 10/1998 | Fogarty et al. |
| 5,824,041 A | 10/1998 | Lenker et al. |
| 5,824,042 A | 10/1998 | Lombardi et al. |
| 5,824,046 A | 10/1998 | Smith et al. |
| 5,827,327 A | 10/1998 | McHaney |
| 5,833,694 A | 11/1998 | Poncet |
| 5,836,926 A | 11/1998 | Peterson et al. |
| 5,843,090 A | 12/1998 | Schuetz |
| 5,843,166 A | 12/1998 | Lentz et al. |
| 5,860,999 A | 1/1999 | Schnepp-Pesch |
| 5,868,755 A | 2/1999 | Kanner et al. |
| 5,876,448 A | 3/1999 | Thompson et al. |
| 5,891,114 A | 4/1999 | Chien et al. |
| 5,897,537 A | 4/1999 | Berg et al. |
| 5,906,606 A | 5/1999 | Chee et al. |
| 5,906,619 A | 5/1999 | Olson et al. |
| 5,911,715 A | 6/1999 | Berg et al. |
| 5,925,075 A | 7/1999 | Myers et al. |
| 5,928,258 A | 7/1999 | Khan et al. |

(56) References Cited

U.S. PATENT DOCUMENTS

| | | |
|---|---|---|
| 5,928,279 A | 7/1999 | Shannon et al. |
| 5,944,727 A | 8/1999 | Ahari et al. |
| 5,951,495 A | 9/1999 | Berg |
| 5,954,651 A | 9/1999 | Berg et al. |
| 5,957,930 A | 9/1999 | Vrba |
| 5,957,949 A | 9/1999 | Leonhardt et al. |
| 5,961,545 A | 10/1999 | Lentz et al. |
| 5,968,052 A | 10/1999 | Sullivan, III et al. |
| 5,968,091 A | 10/1999 | Pinchuk et al. |
| 5,980,533 A | 11/1999 | Holman |
| 5,984,964 A | 11/1999 | Roberts et al. |
| 6,001,125 A | 12/1999 | Golds et al. |
| 6,010,529 A | 1/2000 | Herweck et al. |
| 6,013,019 A | 1/2000 | Fischell et al. |
| 6,019,778 A | 2/2000 | Wilson et al. |
| 6,022,374 A | 2/2000 | Imran |
| 6,024,763 A | 2/2000 | Lenker et al. |
| 6,042,578 A | 3/2000 | Dinh |
| 6,042,588 A | 3/2000 | Munsinger et al. |
| 6,042,589 A | 3/2000 | Marianne |
| 6,042,606 A | 3/2000 | Frantzen |
| 6,053,941 A | 4/2000 | Lindenberg |
| 6,056,759 A | 5/2000 | Fiedler |
| 6,070,589 A | 6/2000 | Keith et al. |
| 6,077,295 A | 6/2000 | Limon et al. |
| 6,083,257 A | 7/2000 | Taylor et al. |
| 6,091,778 A | 7/2000 | Sporer |
| 6,110,198 A | 8/2000 | Fogarty et al. |
| 6,113,608 A | 9/2000 | Monroe et al. |
| 6,120,522 A | 9/2000 | Vrba et al. |
| 6,123,722 A | 9/2000 | Fogarty et al. |
| 6,124,523 A | 9/2000 | Banas |
| 6,126,685 A | 10/2000 | Lenker et al. |
| 6,129,755 A | 10/2000 | Mathis et al. |
| 6,132,458 A | 10/2000 | Staehle et al. |
| 6,136,006 A | 10/2000 | Johnson et al. |
| 6,139,524 A | 10/2000 | Killion |
| 6,139,573 A | 10/2000 | Sogard et al. |
| 6,143,013 A | 11/2000 | Samson et al. |
| 6,143,016 A | 11/2000 | Bleam et al. |
| 6,143,021 A | 11/2000 | Staehle |
| 6,146,389 A | 11/2000 | Geitz |
| 6,146,415 A | 11/2000 | Fitz |
| 6,149,680 A | 11/2000 | Shelso et al. |
| 6,165,210 A | 12/2000 | Lau et al. |
| 6,165,211 A | 12/2000 | Thompson |
| 6,165,213 A | 12/2000 | Goicoechea et al. |
| 6,168,617 B1 | 1/2001 | Blaeser et al. |
| 6,174,327 B1 | 1/2001 | Mertens et al. |
| 6,176,875 B1 | 1/2001 | Lenker et al. |
| 6,183,481 B1 | 2/2001 | Lee et al. |
| 6,190,393 B1 | 2/2001 | Bevier et al. |
| 6,190,403 B1 | 2/2001 | Fischell et al. |
| 6,193,745 B1 | 2/2001 | Fogarty et al. |
| 6,203,550 B1 | 3/2001 | Olson |
| 6,203,568 B1 | 3/2001 | Lombardi et al. |
| 6,206,888 B1 | 3/2001 | Bicek et al. |
| 6,212,422 B1 | 4/2001 | Berg |
| 6,217,586 B1 | 4/2001 | Mackenzie |
| 6,217,609 B1 | 4/2001 | Haverkost |
| 6,221,081 B1 | 4/2001 | Mikus et al. |
| 6,228,110 B1 | 5/2001 | Munsinger |
| 6,231,598 B1 | 5/2001 | Berry et al. |
| 6,238,402 B1 | 5/2001 | Sullivan, III et al. |
| 6,238,410 B1 | 5/2001 | Vrba et al. |
| 6,238,430 B1 | 5/2001 | Klumb et al. |
| 6,241,758 B1 | 6/2001 | Cox |
| 6,245,098 B1 | 6/2001 | Feeser et al. |
| 6,245,099 B1 | 6/2001 | Edwin et al. |
| 6,245,100 B1 | 6/2001 | Davila et al. |
| 6,251,132 B1 | 6/2001 | Ravenscroft et al. |
| 6,254,608 B1 | 7/2001 | Solar |
| 6,254,609 B1 | 7/2001 | Vrba et al. |
| 6,254,611 B1 | 7/2001 | Vrba |
| 6,264,671 B1 | 7/2001 | Stack et al. |
| 6,270,523 B1 | 8/2001 | Herweck et al. |
| 6,270,525 B1 | 8/2001 | Letendre et al. |
| 6,280,465 B1 | 8/2001 | Cryer |
| 6,280,467 B1 | 8/2001 | Leonhardt |
| 6,287,315 B1 | 9/2001 | Wijeratne et al. |
| 6,287,329 B1 | 9/2001 | Duerig et al. |
| 6,293,966 B1 | 9/2001 | Frantzen |
| 6,296,661 B1 | 10/2001 | Davila et al. |
| 6,302,893 B1 | 10/2001 | Limon et al. |
| 6,306,141 B1 | 10/2001 | Jervis |
| 6,306,145 B1 | 10/2001 | Leschinsky |
| 6,312,455 B2 | 11/2001 | Duerig et al. |
| 6,312,456 B1 | 11/2001 | Kranz et al. |
| 6,315,791 B1 | 11/2001 | Gingras et al. |
| 6,331,186 B1 | 12/2001 | Wang et al. |
| 6,334,869 B1 | 1/2002 | Leonhardt et al. |
| 6,336,938 B1 | 1/2002 | Kavteladze et al. |
| 6,350,278 B1 | 2/2002 | Lenker et al. |
| 6,352,553 B1 | 3/2002 | van der Burg et al. |
| 6,352,561 B1 | 3/2002 | Leopold et al. |
| 6,355,057 B1 | 3/2002 | DeMarais et al. |
| 6,355,060 B1 | 3/2002 | Lenker et al. |
| 6,361,555 B1 | 3/2002 | Wilson |
| 6,368,344 B1 | 4/2002 | Fitz |
| 6,371,979 B1 | 4/2002 | Beyar et al. |
| 6,375,676 B1 | 4/2002 | Cox |
| 6,380,457 B1 | 4/2002 | Yurek et al. |
| 6,383,211 B1 | 5/2002 | Staehle |
| 6,383,214 B1 | 5/2002 | Banas |
| 6,383,216 B1 | 5/2002 | Kavteladze et al. |
| 6,387,117 B1 | 5/2002 | Arnold, Jr. et al. |
| 6,387,118 B1 | 5/2002 | Hanson |
| 6,391,033 B2 | 5/2002 | Ryan |
| 6,391,051 B2 | 5/2002 | Sullivan, III et al. |
| 6,398,802 B1 | 6/2002 | Yee |
| 6,413,269 B1 | 7/2002 | Bui et al. |
| 6,425,898 B1 | 7/2002 | Wilson et al. |
| 6,432,127 B1 | 8/2002 | Kim et al. |
| 6,432,129 B2 | 8/2002 | DiCaprio |
| 6,436,135 B1 | 8/2002 | Goldfarb |
| 6,436,214 B1 | 8/2002 | Murata |
| 6,443,979 B1 | 9/2002 | Stalker et al. |
| 6,468,298 B1 | 10/2002 | Pelton |
| 6,471,718 B1 | 10/2002 | Staehle et al. |
| 6,482,211 B1 | 11/2002 | Choi |
| 6,482,227 B1 | 11/2002 | Solovay |
| 6,488,694 B1 | 12/2002 | Lau et al. |
| 6,488,701 B1 | 12/2002 | Nolting et al. |
| 6,503,271 B2 | 1/2003 | Duerig et al. |
| 6,503,353 B1 | 1/2003 | Peterson et al. |
| 6,505,066 B2 | 1/2003 | Berg et al. |
| 6,506,066 B2 | 1/2003 | Kuki |
| 6,514,280 B1 | 2/2003 | Gilson |
| 6,514,283 B2 | 2/2003 | DiMatteo et al. |
| 6,517,547 B1 | 2/2003 | Feeser et al. |
| 6,517,569 B2 | 2/2003 | Mikus et al. |
| 6,517,570 B1 | 2/2003 | Lau et al. |
| 6,517,571 B1 | 2/2003 | Brauker et al. |
| 6,520,983 B1 | 2/2003 | Colgan et al. |
| 6,520,986 B2 | 2/2003 | Martin et al. |
| 6,524,334 B1 | 2/2003 | Thompson |
| 6,530,947 B1 | 3/2003 | Euteneuer et al. |
| 6,554,841 B1 | 4/2003 | Yang |
| 6,572,647 B1 | 6/2003 | Supper et al. |
| 6,576,006 B2 | 6/2003 | Limon et al. |
| 6,582,460 B1 | 6/2003 | Cryer |
| 6,592,569 B2 | 7/2003 | Bigus et al. |
| 6,592,614 B2 | 7/2003 | Lenker et al. |
| 6,602,280 B2 | 8/2003 | Chobotov |
| 6,605,109 B2 | 8/2003 | Fiedler |
| 6,613,072 B2 | 9/2003 | Lau et al. |
| 6,613,079 B2 | 9/2003 | Wolinsky et al. |
| 6,613,081 B2 | 9/2003 | Kim et al. |
| 6,623,518 B2 | 9/2003 | Thompson et al. |
| 6,626,934 B2 | 9/2003 | Blaeser et al. |
| 6,626,938 B1 | 9/2003 | Butaric et al. |
| 6,626,992 B2 | 9/2003 | Vijn et al. |
| 6,629,992 B2 | 10/2003 | Bigus et al. |
| 6,641,606 B2 | 11/2003 | Ouriel et al. |

(56) References Cited

U.S. PATENT DOCUMENTS

| | | |
|---|---|---|
| 6,652,570 B2 | 11/2003 | Smith et al. |
| 6,656,212 B2 | 12/2003 | Ravenscroft et al. |
| 6,656,213 B2 | 12/2003 | Solem |
| 6,656,215 B1 | 12/2003 | Yanez et al. |
| 6,660,031 B2 | 12/2003 | Tran et al. |
| 6,673,102 B1 | 1/2004 | Vonesh et al. |
| 6,673,103 B1 | 1/2004 | Golds et al. |
| 6,673,105 B1 | 1/2004 | Chen |
| 6,676,666 B2 | 1/2004 | Vrba et al. |
| 6,676,693 B1 | 1/2004 | Belding et al. |
| 6,689,120 B1 | 2/2004 | Gerdts |
| 6,695,862 B2 | 2/2004 | Cox et al. |
| 6,699,274 B2 | 3/2004 | Stinson |
| 6,709,454 B1 | 3/2004 | Cox et al. |
| 6,709,455 B1 | 3/2004 | Chouinard |
| 6,716,239 B2 | 4/2004 | Sowinski et al. |
| 6,726,712 B1 | 4/2004 | Raeder-Devens |
| 6,726,714 B2 | 4/2004 | DiCaprio et al. |
| 6,733,521 B2 | 5/2004 | Chobotov et al. |
| 6,736,839 B2 | 5/2004 | Cummings |
| 6,743,210 B2 | 6/2004 | Hart et al. |
| 6,743,219 B1 | 6/2004 | Dwyer et al. |
| 6,755,854 B2 | 6/2004 | Gillick et al. |
| 6,755,855 B2 | 6/2004 | Yurek et al. |
| 6,761,733 B2 | 7/2004 | Chobotov et al. |
| 6,767,358 B2 | 7/2004 | Leonhardt et al. |
| 6,773,446 B1 | 8/2004 | Dwyer et al. |
| 6,780,199 B2 | 8/2004 | Solar et al. |
| 6,786,918 B1 | 9/2004 | Krivoruchko et al. |
| 6,786,920 B2 | 9/2004 | Shannon et al. |
| 6,790,221 B2 | 9/2004 | Monroe et al. |
| 6,790,225 B1 | 9/2004 | Shannon et al. |
| 6,824,553 B1 | 11/2004 | Samson et al. |
| 6,827,731 B2 | 12/2004 | Armstrong et al. |
| 6,833,002 B2 | 12/2004 | Stack et al. |
| 6,843,802 B1 | 1/2005 | Villalobos et al. |
| 6,852,116 B2 | 2/2005 | Leonhardt et al. |
| 6,884,260 B2 | 4/2005 | Kugler et al. |
| 6,887,268 B2 | 5/2005 | Butaric et al. |
| 6,890,349 B2 | 5/2005 | McGuckin, Jr. et al. |
| 6,942,692 B2 | 9/2005 | Landau et al. |
| 7,758,624 B2 | 7/2010 | Dorn et al. |
| 8,043,364 B2 | 10/2011 | Lombardi et al. |
| 2001/0034549 A1 | 10/2001 | Bartholf et al. |
| 2002/0016597 A1 | 2/2002 | Dwyer et al. |
| 2002/0058985 A1 | 5/2002 | DePalma et al. |
| 2002/0058986 A1 | 5/2002 | Landau et al. |
| 2002/0058993 A1 | 5/2002 | Landau et al. |
| 2002/0065546 A1 | 5/2002 | Machan et al. |
| 2002/0120323 A1 | 8/2002 | Thompson et al. |
| 2002/0138129 A1 | 9/2002 | Armstrong et al. |
| 2002/0183826 A1 | 12/2002 | Dorn et al. |
| 2003/0028240 A1 | 2/2003 | Nolting et al. |
| 2003/0040789 A1 | 2/2003 | Colgan et al. |
| 2003/0050686 A1 | 3/2003 | Raeder-Devens et al. |
| 2003/0083623 A1 | 5/2003 | Berg et al. |
| 2003/0195490 A1 | 10/2003 | Boatman et al. |
| 2004/0015228 A1 | 1/2004 | Lombardi et al. |
| 2004/0098092 A1 | 5/2004 | Butaric et al. |
| 2004/0122360 A1 | 6/2004 | Waldhauser et al. |
| 2004/0127912 A1 | 7/2004 | Rabkin et al. |
| 2004/0199241 A1 | 10/2004 | Gravett et al. |
| 2004/0215318 A1 | 10/2004 | Kwitkin |
| 2004/0236403 A1 | 11/2004 | Leonhardt et al. |
| 2005/0021002 A1* | 1/2005 | Deckman et al. ............ 604/527 |
| 2005/0021126 A1 | 1/2005 | Machan et al. |
| 2005/0131515 A1 | 6/2005 | Cully et al. |
| 2005/0171594 A1 | 8/2005 | Machan et al. |
| 2006/0116625 A1 | 6/2006 | Renati et al. |
| 2006/0173528 A1 | 8/2006 | Feld et al. |
| 2007/0067024 A1 | 3/2007 | White et al. |
| 2007/0142894 A1 | 6/2007 | Moore et al. |
| 2007/0173921 A1 | 7/2007 | Wholey et al. |
| 2007/0198078 A1 | 8/2007 | Berra et al. |
| 2007/0203566 A1 | 8/2007 | Arbefeuille et al. |
| 2007/0265697 A1 | 11/2007 | Goicoechea et al. |
| 2008/0015682 A1 | 1/2008 | Majercak et al. |

FOREIGN PATENT DOCUMENTS

| | | |
|---|---|---|
| CA | 2608160 A1 | 1/2007 |
| DE | 19838414 A1 | 3/2000 |
| EP | 0033659 A2 | 8/1981 |
| EP | A-119 688 | 9/1984 |
| EP | 0277366 A1 | 8/1988 |
| EP | 0408245 A1 | 1/1991 |
| EP | A-554 579 | 8/1993 |
| EP | 0596145 A1 | 5/1994 |
| EP | 0653924 A1 | 5/1995 |
| EP | 0686379 A2 | 12/1995 |
| EP | 0696447 A2 | 2/1996 |
| EP | A-720 837 | 7/1996 |
| EP | 0744164 A1 | 11/1996 |
| EP | 0747021 A2 | 12/1996 |
| EP | A-747 022 | 12/1996 |
| EP | 0775372 A1 | 5/1997 |
| EP | 0775470 A1 | 5/1997 |
| EP | 0788332 A1 | 8/1997 |
| EP | 0792627 A2 | 9/1997 |
| EP | 0792656 A1 | 9/1997 |
| EP | A-819 411 | 1/1998 |
| EP | 0821574 A1 | 2/1998 |
| EP | A-850 655 | 7/1998 |
| EP | 0858299 A1 | 8/1998 |
| EP | 0935976 A1 | 8/1999 |
| EP | 0941716 A2 | 9/1999 |
| EP | 0943302 A2 | 9/1999 |
| EP | A-948 946 | 10/1999 |
| EP | 1010406 A2 | 6/2000 |
| EP | 1025813 A2 | 8/2000 |
| EP | 1095634 A2 | 5/2001 |
| EP | 1121174 A1 | 8/2001 |
| EP | 1129674 A1 | 9/2001 |
| EP | 1199051 A2 | 4/2002 |
| EP | 1210033 A1 | 6/2002 |
| EP | 1338253 A1 | 8/2003 |
| EP | 1879520 A2 | 1/2008 |
| GB | 1033971 A | 6/1966 |
| GB | 2043201 A | 10/1980 |
| JP | 09-84880 A | 5/1976 |
| JP | 62-82976 A | 4/1987 |
| JP | 1-291875 A | 11/1989 |
| JP | 2920541 A | 5/1991 |
| JP | 04-40652 U | 4/1992 |
| JP | 04-183478 A | 6/1992 |
| JP | 05-43392 | 7/1993 |
| JP | 05-84303 U | 11/1993 |
| JP | 08-141090 A | 6/1996 |
| JP | 08-196642 A | 8/1996 |
| JP | 09-173467 A | 7/1997 |
| JP | 10-305050 A | 11/1998 |
| JP | 2001327609 A | 11/2001 |
| JP | 2002-102357 A | 4/2002 |
| JP | 2002282367 A | 10/2002 |
| JP | 2003-516718 A | 5/2003 |
| JP | 2008539928 A | 11/2008 |
| JP | 4917089 B2 | 4/2012 |
| WO | 9219308 A1 | 11/1992 |
| WO | 9308986 A1 | 5/1993 |
| WO | 9315785 A1 | 8/1993 |
| WO | 9320881 A1 | 10/1993 |
| WO | 9417754 A1 | 8/1994 |
| WO | 9505132 A1 | 2/1995 |
| WO | 9532688 A1 | 12/1995 |
| WO | 9600103 A1 | 1/1996 |
| WO | 9619255 A1 | 6/1996 |
| WO | 9620750 A1 | 7/1996 |
| WO | 9628115 A1 | 9/1996 |
| WO | 9633672 A1 | 10/1996 |
| WO | 9639998 A2 | 12/1996 |
| WO | 9709932 A1 | 3/1997 |
| WO | WO 99/49929 | 3/1998 |
| WO | 9812988 A1 | 4/1998 |

(56) References Cited

FOREIGN PATENT DOCUMENTS

| | | |
|---|---|---|
| WO | 9904728 A1 | 2/1999 |
| WO | 9915108 A2 | 4/1999 |
| WO | 9916387 A1 | 4/1999 |
| WO | 9938455 A1 | 8/1999 |
| WO | 9944541 A1 | 9/1999 |
| WO | 9947075 A1 | 9/1999 |
| WO | 9949808 A1 | 10/1999 |
| WO | 0002503 A1 | 1/2000 |
| WO | 0018330 A1 | 4/2000 |
| WO | 0045742 A1 | 8/2000 |
| WO | 0069368 A2 | 11/2000 |
| WO | 0110492 A1 | 2/2001 |
| WO | 0132102 A1 | 5/2001 |
| WO | 0147436 A2 | 7/2001 |
| WO | 0154614 A2 | 8/2001 |
| WO | 0164134 A1 | 9/2001 |
| WO | 0215820 A2 | 2/2002 |
| WO | 0222053 A2 | 3/2002 |
| WO | 02056798 A2 | 7/2002 |
| WO | 03002018 A2 | 1/2003 |
| WO | 03002019 A2 | 1/2003 |
| WO | 03002020 A2 | 1/2003 |
| WO | 03002033 A1 | 1/2003 |
| WO | 03030783 A1 | 4/2003 |
| WO | 03045275 A2 | 6/2003 |
| WO | 03057298 A2 | 7/2003 |
| WO | 03090644 A1 | 11/2003 |
| WO | 2004004597 A2 | 1/2004 |
| WO | 2004017865 A1 | 3/2004 |
| WO | 2004043301 A1 | 5/2004 |
| WO | WO 2004/062458 | 7/2004 |
| WO | WO 2004/096091 | 11/2004 |
| WO | 2007004076 A2 | 1/2007 |

OTHER PUBLICATIONS

PCT/IB2006/002582 filed May 5, 2006 International Preliminary Report on Patentability dated Nov. 14, 2007.
PCT/IB2006/002582 filed May 5, 2006 Search Report dated Mar. 19, 2007.
PCT/IB2006/002582 filed May 5, 2006 Written Opinion dated Mar. 19, 2007.
EP 06795519.5 filed May 5, 2006 Office Action dated Jun. 24, 2011.
JP 2008-510674 filed Nov. 13, 2000 Office Action dated Apr. 14, 2011.

* cited by examiner

US 8,652,193 B2

IMPLANT DELIVERY DEVICE

PRIORITY DATA AND INCORPORATION BY REFERENCE

This application is a 371 of PCT/IB2006/002582, filed May 5, 2006, which claims priority to U.S. Provisional Patent Application Ser. No. 60/679,025, filed May 9, 2005, the entireties of which are hereby incorporated by reference.

FIELD OF THE INVENTION

This invention relates to a delivery device for an implantable device (e.g., stents, and stent grafts). Such device may include a sheath having an outside surface along a length which includes a proximal portion, a shaft portion and a distal portion, a distal end, a proximal end and a lumen which connects the ends and is adapted to receive a biological implant device through the proximal end and guide the implant to the distal end for deployment into a bodily lumen by expulsion from the distal end of the lumen. Broadly, the invention is concerned with a percutaneous and transluminal guide catheter.

BACKGROUND OF THE INVENTION

U.S. Pat. No. 4,580,568, Gianturco shows a stainless steel stent made of zigzag loops of stainless steel wire. Such stents have come to be known as "Z-stents". The delivery system for Gianturco includes a catheter with a tapered tip, fitted within a sheath.

EP-A-819 411 shows a self-expanding stent between a bed on an inner tube and a sleeve surface on an outer tube, release of the stent being effected by proximal withdrawal of the outer sleeve. The drawings show the distal end of the delivery system abrupt and flat. As described in EP-A-819 411, the event of deployment of the stent is followed by proximal withdrawal, from within the stent envelope, of the inner tube. In EP-A-819 411, the inner tube component of the delivery system, inside the stent envelope, has re-entrant surfaces associated with the bed in which the stent was originally confined. It is believed that any such re-entrant surfaces should be avoided, if at all possible.

U.S. Pat. No. 5,833,694 shows, in FIG. 20, a variation in which the delivery catheter has a uniform diameter and within it a pusher tube 22, the distal end 190 of which serves as a stop for the proximal end of the stent. To deploy the stent, the sheath is pulled back proximally while the distal end of the inner tube prevents proximal movement of the stent itself.

U.S. Pat. No. 5,782,855 Lau et al., shows a stent lying radially between an outer sheath and a balloon catheter. On the distal tip of the balloon catheter is a cone, into which is tucked a tapered distal tip of the outer sheath. For deployment of the stent, the sheath is withdrawn proximally with respect to the stent. After balloon expansion of the stent, the balloon catheter is withdrawn proximally so that the cone passes in the proximal direction the full length of the stent lumen. The cone has an exposed proximal-facing rim edge as it passes through the stent lumen.

U.S. Pat. No. 6,019,778 shows a delivery apparatus for a self-expanding shape memory alloy stent, which features a stent bed on an inner shaft and an outer sheath, which includes a braided reinforcing layer. There is a stop on the shaft member, proximal of the stent bed, to prevent proximal movement of the stent when the outer sheath is withdrawn proximally to release the stent. The braided reinforcement layer is preferably made from stainless steel and is stated to resist a tendency of the stent to become imbedded within the sheath, which surrounds it.

EP-A-720 837 shows an integrated double-function catheter system for balloon angioplasty and stent delivery. An outer sheath with a conically-shaped distal tip portion surrounds a stent. Radially inside the stent is a balloon catheter. The balloon is located well distal of the stent so as to allow better trackability of the distal end of the catheter over a flexible guide wire and through tortuous coronary arteries and through a long tight stenosis.

EP-A-554 579 shows a stent delivery device with coaxial shaft and sheath for a self-expanding stent. The sheath is provided at its distal tip with a protective tip, which is bonded to the sheath thermally or with adhesive, or can be made integral with the sheath. This tip is said to reduce the likelihood of injury to the bodily lumen wall during advancement of the catheter in the lumen.

EP-A-119 688 shows a process and apparatus for restoring patency to bodily vessels in which a shape memory alloy wire is contained within an outer sheath and is abutted at its proximal end by a pushing shaft. It is believed to be deployed by withdrawing the sheath proximally. The diameter of the sheath surrounding the prosthesis is very much greater than the diameter of the sheath for the remainder of its transluminal length, over which it is a relatively snug fit with the pushing shaft. The sheath is said to be inserted, as by conventional techniques, into the aorta of the patient, in order that the prosthesis can be placed at an aneurysm.

U.S. Pat. No. 4,665,918 shows an example of a delivery system for a self-expanding stent held within a surrounding sleeve, which is proximally withdrawn relative to a stent bed in a coaxial inner shaft, and with a tapered tip zone on the shaft, which protrudes beyond the distal end of the surrounding sleeve.

U.S. Pat. No. 5,662,703 shows a delivery device for a self-expanding stent, having an outer catheter surrounding an inner catheter and a tubular stent-retaining sheath formed of a rolling membrane. The self-expanding stent is located at the distal ends of the inner and outer catheters. The stent is radially inwardly constrained by a double-walled rollable membrane. The separate proximal ends of the radially inner and outer membrane portions are fixed respectively to inner and outer catheter components whereas the contiguous-distal ends of the membrane portions converge and narrow thereby to form a tapered tip. For stent release, the outer catheter is moved proximally at least twice the length of the stent in order to pull back proximally both the inner and outer layers of the membrane, thereby releasing the stent.

U.S. Pat. No. 5,735,859 shows a stent delivery device having an inner and outer catheter and a stent covered by a thin-walled sheath. The inner catheter projects beyond the distal end being fixed to the distal end of the outer catheter. The distal end of the sheath is releasably received in the distal section of the inner catheter distal to the stent. The sheath can be released from the distal section of the inner catheter and pulled back from the stent, thereby releasing said stent. Where the distal end of the sheath is received in the distal section of the inner catheter, a step in the radially outside surface of the inner catheter is present.

EP-A-747 022 shows a coil-reinforced retractable sleeve for a stent delivery catheter. One embodiment of the sleeve has a distal tip, which tapers inwardly and is provided with a plurality of slits, which extend proximally from the distal end of the sleeve and substantially parallel to the longitudinal axis of the sleeve, the slits functioning to provide the sleeve with a low profile adapted for traveling through a blood vessel.

EP-A-948 946 shows apparatus and methods for deployment and release of an intraluminal graft for treating a stenosis, the graft being surrounded by a cylindrical cover which is withdrawn proximally to release the graft. The cover can have an atraumatic distal end of reduced diameter in which there are slits extending axially from the distal end wall.

WO 99/49929 shows a rapid exchange delivery system to alleviate a stenosis in a body lumen, with the stent being covered by a retractable sheath, and the stent itself being mounted on a balloon. In the drawings, it appears that the diameter of the sheath is somewhat greater radially outside the stent than in a distal end zone of the sheath, distal of the stent, touching the underlying balloon.

EP-A-850 655 shows a catheter tip mold and cut process in which the molding process creates a flash which extends beyond the desired catheter tip, which flash is then parted from the distal end of the molded catheter tip by use of a cutter.

U.S. Pat. No. 5,843,090 shows an inner catheter with a step at its distal end when the outer catheter is withdrawn proximally. See FIG. 6

U.S. Pat. No. 5,743,874 also shows an inner catheter with a step in its outer surface. See FIG. 1, feature 81.

U.S. Pat. No. 6,726,712 shows a device 16 with a flexible outer catheter 18 with a marker 22 mounted to the catheter. The catheter has distal region 26 with two polymeric materials. A braid 34 is provided at one region of the catheter. The catheter has an outer layer, medial layer and a proximal outer layer which are bonded to a PTFE liner.

U.S. Pat. No. 4,898,591 shows a body 22 with an inner layer 30 and outer layer 32 with a reinforcing braid 34 disposed therebetween. The inner and outer layers 30 and 32 are formed from a blend, i.e., a mixture or intermingling of components, of Nylon and ester-linked polyether-polyamide copolymer in proportions selected to produce desired properties for the catheter.

U.S. Pat. No. 6,042,578 shows an intravascular catheter having an elongated tubular body formed with polymeric materials but no radio-opaque marker or filler due to the presence of a metallic reinforcing braiding.

U.S. Pat. Nos. 5,603,705 and 5,674,208 show an intravascular catheter with inner and outer tubular members provided with a support member formed from wire braiding.

U.S. Pat. Nos. 5,951,495 and 5,951,495 show the use of various adhesives to restrain the flaring of wire braiding in a catheter.

U.S. Pat. No. 6,212,422 shows a catheter with an inner member, outer member and a tubular braid layer therebetween. A braid restraint is also shown and described.

U.S. Pat. No. 6,505,066 shows a catheter with a lubricious liner and a wire braiding with adhesive means to restrain the free ends from flaring.

The documents described above are incorporated by reference herein in their entirety.

SUMMARY OF THE PRESENT INVENTION

The present invention provides a medical implant delivery device. The implant delivery device can include one of a stent and a stent graft. In one aspect, the present invention provides a system for delivering stents to stenosis or other sites within a biological body of a patient, which minimizes trauma to the affected tissue of the patient yet, at the same time, offers the medical practitioner a robust and simple system for stent placement. In one preferred embodiment, an implant delivery device includes a first shaft having a proximal portion and a distal portion. The first shaft has an outer surface and an inner surface defining a first lumen along a longitudinal axis and the distal portion has a tip defining a taper in the distal direction toward the longitudinal axis and terminating at a distal opening. The device includes a second shaft having a proximal portion and a distal portion and an inner surface defining a second lumen therebetween having a first cross-section. The second shaft is preferably disposed within the first lumen such that the second lumen is generally coaxial with the first lumen to define a chamber. The distal portion of the second shaft preferably terminates in a port having an opening in communication with the distal opening of the first shaft. The port preferably has a second cross-section greater than the first cross-section. The port can include a flared portion extending in a direction toward the inner surface of the first shaft. Moreover, at least a portion of the port can be substantially frusto-conical. Preferably the flared portion circumscribes the longitudinal axis such that at least a portion of the port is substantially tulip-shaped.

In another embodiment of the implant delivery device, the device includes an outer sheath having a proximal end and a distal end. The outer sheath has an inner surface defining a lumen along a longitudinal axis. The device also includes an inner shaft having a proximal portion and a distal portion, the inner shaft disposed within the lumen to define a chamber between the outer sheath and the inner shaft. The inner shaft is movable along the longitudinal axis relative to the outer sheath. The device further includes a member disposed between the inner shaft and the outer sheath. The member has a surface movable relative to the inner shaft and outer sheath. The member preferably provides a pusher. In another aspect, the present invention provides a sheath, which is, at the same time, both a guide catheter and an outer sheath for a delivery system for an implant (such as a stent). The sheath preferably surrounds the pusher wherein operation, the pusher becomes a stationary pusher. The pusher being coupled to a coiled spring disposed within a portion of the sheath.

According to yet another aspect, the delivery device includes an inner shaft coupled to a truncated tulip portion disposed within an outer catheter shaft. The inner shaft extends within the outer sheath to receive a guide wire. According to yet another aspect, the delivery device includes an outer sheath connected to a tip at one distal portion of the outer sheath. The outer sheath includes a proximal portion having a flared end coupled to an introducer having a swivel nut. The flared end is bonded to an inner surface of the swivel nut and disposed between the swivel nut and a boss. In a further aspect, a locking mechanism is provided between at least one of the inner catheter, swivel nut, boss, and a fluid manifold to prevent extraction proximally of the inner catheter through at least one of the swivel nut, boss, or fluid manifold.

In yet another embodiment of the implant delivery device, the device includes an inner shaft having a proximal end and a distal end spaced apart along a longitudinal axis, and an outer sheath disposed about the inner shaft. The outer sheath is movable along the longitudinal axis relative to the inner shaft. The outer sheath has a layer including a proximal portion, a distal portion, and at least one intermediate portion therebetween. The proximal, distal and at least one intermediate portions are preferably discrete portions along the longitudinal axis, each having a discrete durometer. Preferably the durometers of the discrete portion increase from the distal portion to the proximal portion.

An alternative embodiment of an implant delivery device includes an inner shaft having a proximal end and a distal end spaced apart along a longitudinal axis, and an outer sheath having a proximal portion, a distal portion and at least one intermediate portion therebetween. The outer sheath is disposed about the inner shaft and is preferably movable along the longitudinal axis relative to the inner shaft. The outer sheath preferably includes an inner layer, an outer layer, an intermediate layer, and a braiding disposed between a portion of the inner and outer layer. The outer layer preferably includes a first polymer; a second polymer having a durometer greater that of the first polymer and at least a third polymer disposed between the first and second polymer to join the braid to the first and second polymer.

Another embodiment of the preferred invention provides a method of forming an outer sheath of an implant delivery device. The method includes forming a tubular membrane with a distal end over a mandrel and withdrawing the mandrel through the distal end. Preferably, the distal end includes a tip such that withdrawing the mandrel includes withdrawing the mandrel through the tip to form an opening in the tip.

Another preferred embodiment provides a catheter sheath. The sheath preferably includes a first polymer material that circumscribes and extends along a longitudinal axis over a first length and a second polymer contiguous to the first polymer that extends along the longitudinal axis along a second length less than the first and having a surface exposed to the longitudinal axis. The sheath further includes a third polymer interposed between the first and second polymer that extends along the longitudinal axis along a third length less than the first length and a marker contiguous to one of the first and second polymers.

In yet another preferred embodiment, a catheter sheath includes a proximal portion, a distal portion and at least one intermediate portion therebetween. The sheath has an inner and an outer layer. The outer layer preferably includes a first polymer, a second polymer having a durometer greater that of the first polymer and at least a third polymer disposed between the first and second polymer to join the braid to the first and second polymer.

In yet a further aspect, the present invention provides for an outer catheter with an outer layer having at least three distinct polymeric regions, each with a different hardness value. In particular, the at least three distinct polymeric regions have successively increasing hardness values, and one of the polymeric regions is joined to a Nylon portion. The outer layers are coupled to an inner layer. Between the two layers, a reinforcement mesh (i.e., braiding) is spaced along the length of the outer catheter substantially closer to the outer surface than to the inner surface. The braided portion can include metallic wires.

In another aspect, the delivery system, according to the preferred embodiments, allows for lower deployment forces with a known stent graft. In particular, for a stent graft 112 with a diameter of 6 mm by 80 mm, the average deployment force is about 23 Newtons ("N"); for a stent graft 112 with a diameter of 7 mm by 60 mm, the average deployment force is less than 17N; for a stent graft 112 with a diameter of 7 mm by 80 mm, the average deployment force is less than 30N and preferably 17N; for a stent graft 112 with a diameter of 10 mm by 80 mm in length, the average deployment force is less than 20N.

According to another aspect of the invention, there is provided a stent delivery device having an outer sheath. The outer sheath is coupled to a truncated generally conical tip having an inner and outer surface spaced apart over a thickness of about 0.2 millimeters at one portion of the tip and about 0.1 millimeter at a distal portion of the tip.

BRIEF DESCRIPTIONS OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Figure 1:
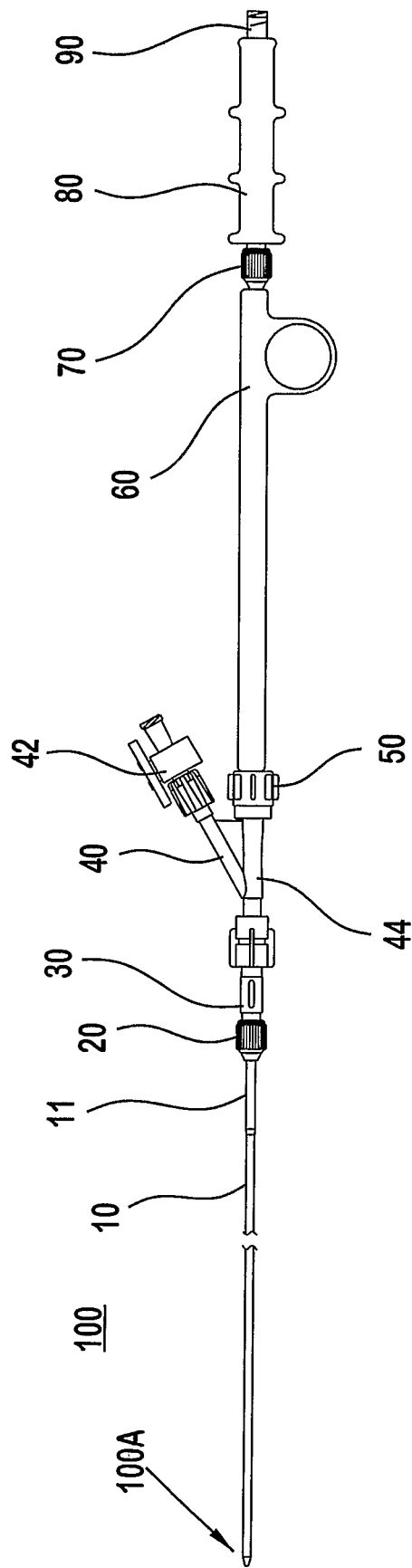
FIG. 1 is a plan view of a preferred embodiment of a delivery device.

FIGS. 1-9 illustrate the preferred embodiments. Referring to FIG. 1, there is shown a preferred embodiment of an implant delivery device 100. The implant delivery device 100 is preferably for delivery of a stent graft 112 or stent (not shown). The delivery device 100 includes an outer sheath 10, swivel nut 20, coupling 30, Y-adapter 40 and a Tuohy-Borst valve 50, safety mechanism 60, coupling 70, adapter body 80, and adapter 90. The delivery device 100 is provided in a plurality of sizes as appropriate for implanting the stent graft 112 or stent in a vessel of a mammal. For example, the device 100 can be configured to have an outer diameter 6, 7, 8, 9, or 10 in "French sizes" with at least two different lengths, 80 centimeters or 120 centimeters. It should be noted that the term "French size" denotes a scale used to identify the outer diameter of a catheter. French scale units are obtained by multiplying the outer diameter of the catheter in millimeter by about 3.0. Likewise, multiplying the French size by about 0.33 will give the outer diameter of the catheter in millimeters ("mm").

The stent graft 112 (for use with the device 100) can be, for example, a vascular stent graft 112 available from Bard Peripheral Vascular Inc., under the trade name "Fluency™," which is shown and described in the brochure entitled "Fluency™ Tracheobronchial Stent Graft," from Bard Peripheral Vascular Inc., having identifier No. S1413A (2003) incorporated by reference herein in its entirety. Alternatively, other self-expanding stent of Nitinol shape memory alloy or balloon expandable stents can be utilized with the device 100. A brochure distributed by Angiomed GmbH & Co. Medizintechnik KG and Bard Peripheral Vascular Inc., entitled: "Fluency™ Vascular Stent Graft: Step By Step Placement," having identifier No. A05000010 (08/2003-R), which is incorporated by reference herein in its entirety, describes placement of the stent graft 112 with a known delivery device. As used herein, the term "stent" includes both "stent grafts" and "stents."

The stent graft 112 is confined within the lumen of an outer sheath 10 surrounding a boss portion 22 and lying radially outside the tubular wall of an inner shaft 14 of the delivery device 100. For deployment of the stent graft 112, the distal end 100A of the delivery device 100 is arranged so that the confined stent graft 112 lies inside the stenosed region 200 to be treated and then, holding the inner shaft 14 against proximal movement, the outer sheath 10 is withdrawn proximally, so as to release the stent graft 112 into the stenosed region (FIG. 8I).

Figure 2:
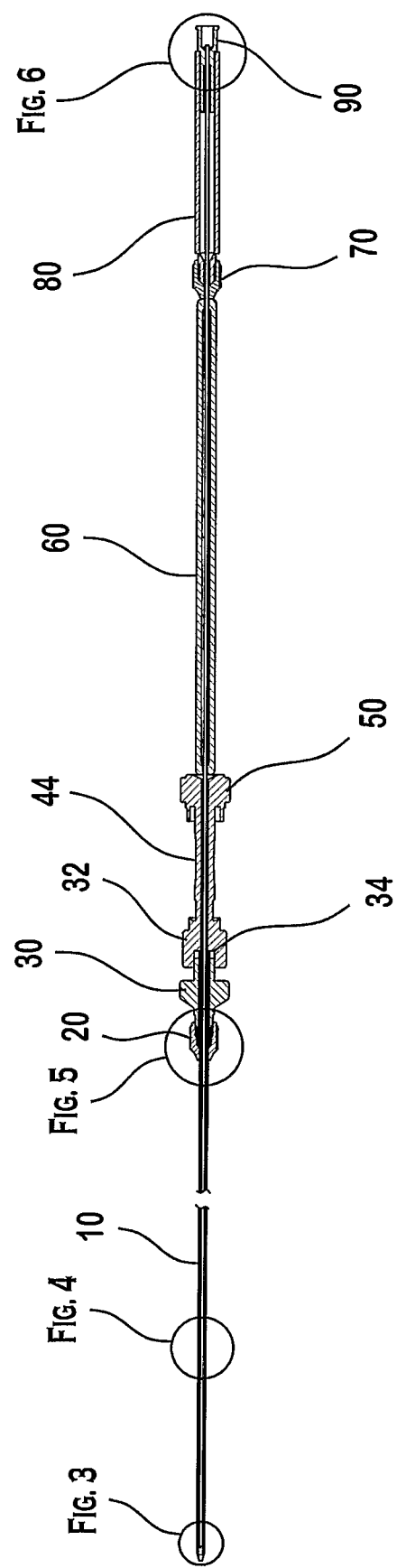
FIG. 2 is a cross-sectional view of the device of FIG. 1 with enlarged views of various portions of the device.
Figure 6:
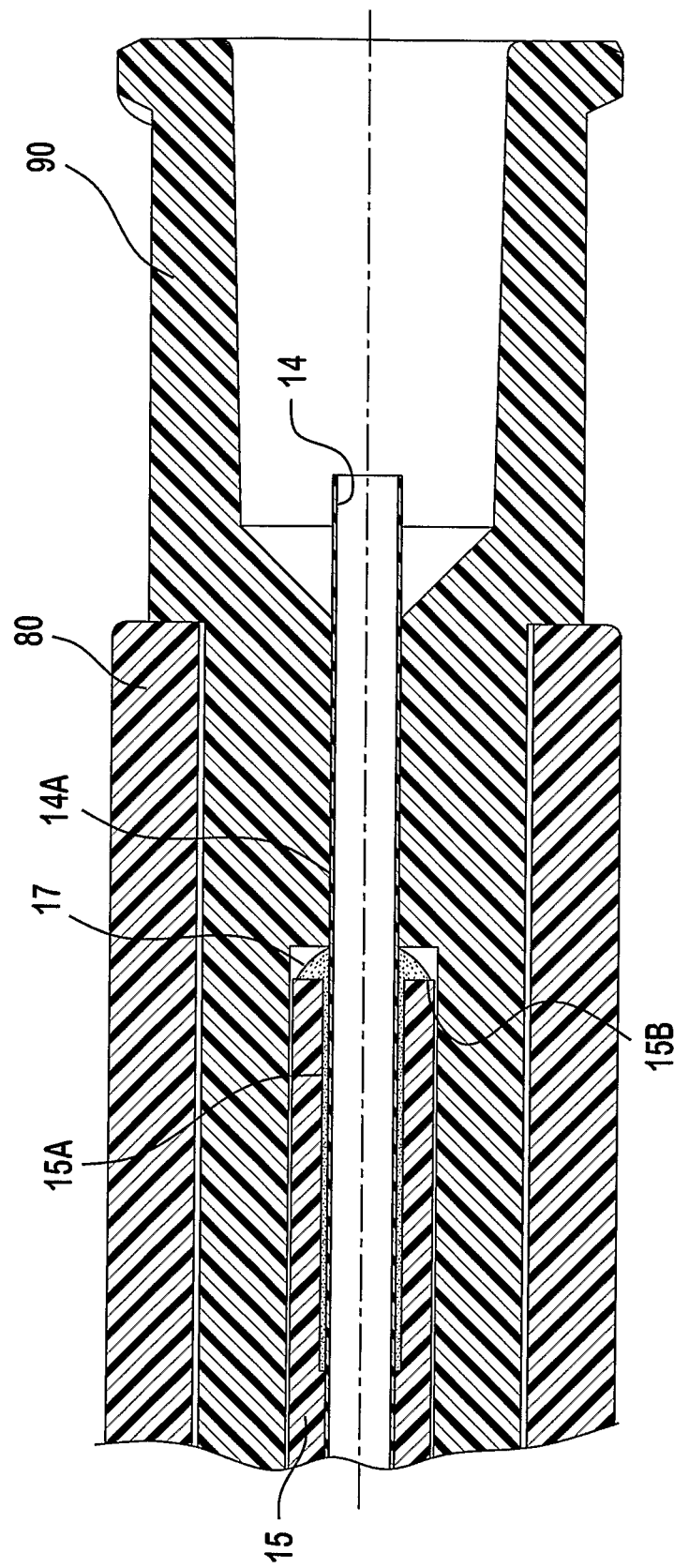
FIG. 6 is an enlarged view of a luer-coupling portion of the device of FIG. 2. The luer-coupling portion includes an inner catheter and a luer-adapter.

The delivery device 100 is shown as a dual-lumen, generally coaxial catheter system that includes an outer sheath 10 (also known as an "outer catheter") and an inner shaft 14 (also known as "an inner catheter"). The outer sheath 10 is attached to a tube end portion 11, which is coupled to a swivel nut 20. The swivel nut 20 is coupled to a boss 30 for mounting a Y-adapter 40, which is connected to a Tuohy-Borst valve 50 at one end of the Y-adapter 40. A clockwise rotation of the valve 50 will gradually prevent rotation of the inner shaft 14 relative to the outer sheath 10. A fluid valve 42 is connected to the other end of the Y-adapter 40. The fluid valve 42 allows the device 100 to be flushed with sterile saline to reduce or eliminate air bubbles and facilitate delivery of the stent graft 112 by allowing fluid for lubrication and clearing out any occlusions. A safety device 60 is provided to maintain the stent graft 112 in a undeployed state in the outer sheath 10. As shown in FIGS. 2 and 6, the inner shaft 14 is attached to the adapter body 80 via a generally stiff tubular member or outer shaft 15. The inner shaft 14 extends for a substantial portion of the outer shaft 15. At a terminal end of the device 100, the body 80 is provided with a luer-adapter 90.

Figure 3:
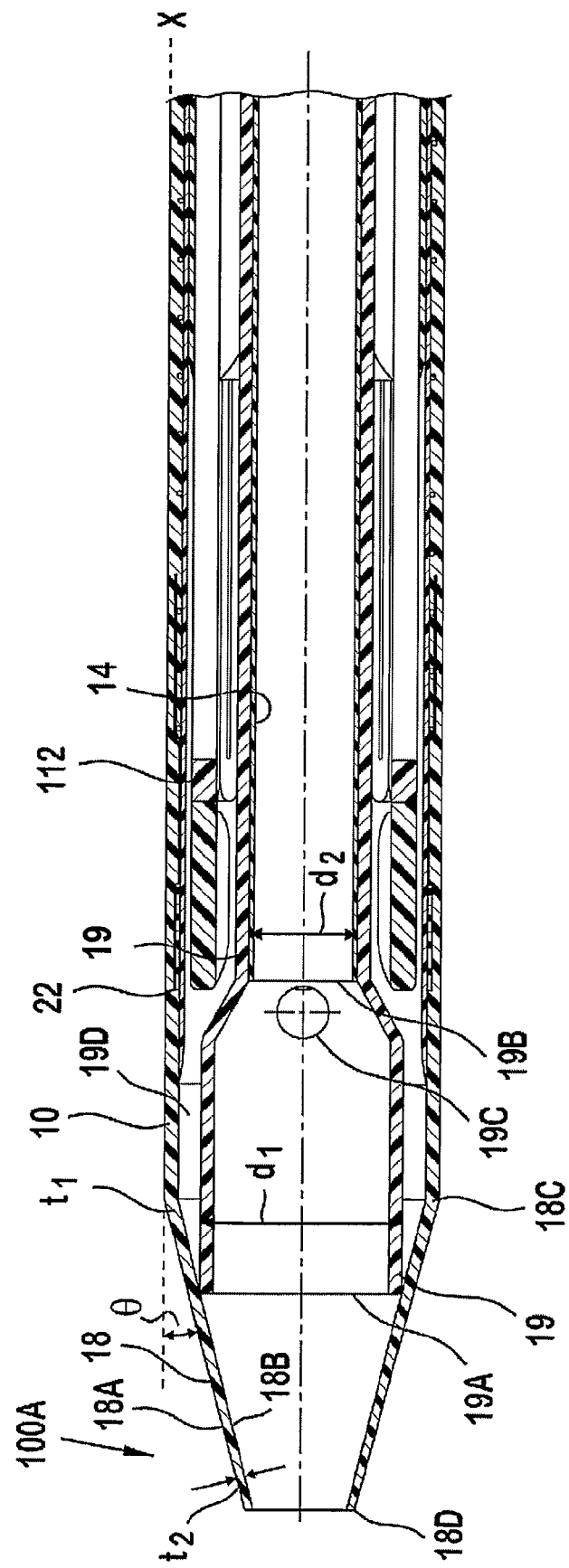
FIG. 3 is an enlarged view of a tip portion of the device of FIG. 2 that illustrates a portion of a stent graft being disposed in the tip portion.

FIG. 3 shows that the distal end 100A of the outer sheath 10 is a tapered tip 18 which can be molded out of the material of the wall of the sheath 10 or of another material, which is most preferably PEBAX® having a durometer value of about 40D. The tip 18 has parallel wall surfaces 18A and 18B, which in a preferred embodiment, a generally constant wall thickness "t" is provided from its base 18C all the way to the distal opening 18D of the tip 18. Not visible in the drawings are two lengthwise slits in the wall thickness of the outer sheath 10, running from the distal opening proximally back over most of the length of the tapered tip 18 and arranged diametrically opposite each other on the tip 18. These slits are believed to reduce the tensile stress needed to pull the outer sheath 10 proximally back over the stent lengthwise during stent deployment.

Disposed partly in the tip 18 is a flared entrant port 19 with first opening 19A defining a first cross-section areas perpendicular to the longitudinal axis of the device 100. The port 19 has a second opening 19B defining a second cross-sectional area perpendicular to the longitudinal axis smaller than the first cross-sectional area. The port 19 preferably includes an aperture 19C for transporting fluid from one end of the device to the tip 18 and vice versa. The entrant port 19 preferably includes a shaft portion disposed about the inner shaft 14 to couple the entrant port 19 to the inner shaft 14. In the preferred embodiments, the largest transverse distance "$d_1$" between the inner surfaces of the distal end 19A is at least 10% greater than the largest transverse distance "$d_2$" between opposing outer surfaces of the inner shaft 14. The entrant port 19 is preferably slidably touching the sheath 10. As shown in FIG. 3, a marker 22 can be provided to indicate the location of a distal end of the stent graft 112. The tip 18, entrant port 19 and the inner shaft 14 are provided with a hollow opening so that an appropriately sized guide wire can be inserted through the tip end 18D to the entrant port 19A and into the inner shaft 14.

In one variation, the wall thickness "t" of the tapered distal tip 18 of the inner shaft 14 is configured to decrease in thickness "$t_1$" from the base 18C towards the final distal opening 18D with thickness "$t_2$." Preferably, the thickness $t_1$ is about 0.2 millimeters and the thickness $t_2$ is about 0.1 millimeters within a range of tolerance that allows for operational use of the delivery device. The decrease between the two positions is generally constant linearly over the axial length of the tip. However, variations in the decrease in thickness as a function of axial length along axis X can also be utilized. The decrease in thickness is believed to be needed in order to accommodate the deformation of the tip 18 during stent deployment via elastic deformation of the distal end of the distal tip 18, rather than by the use of slits, as is the case described above. The tip 18 angle θ with respect axis X is preferably in a range about 8 degrees to about 20 degrees. Marker 22 can be an annular member having preferably about 90% platinum and about 10% iridium alloy being secured to the outer sheath 10. The marker 22 can also be a suitable material made radio-opaque (i.e., visible under X-rays) by doping the material, for example, with barium sulfate. In the preferred embodiments, the wall thickness "$t_3$" of the intermediate outer sheath 10 is about 0.2 millimeters; the wall thickness "$t_4$" is about 0.2 millimeters; the wall thickness "$t_5$" is about 0.3 millimeters. As used herein, variations in the values provided in the preferred embodiment are possible as long as the variations in the given values allow for the catheter sheath 10 to perform for its intended function as part of a delivery device 100.

Figure 4:
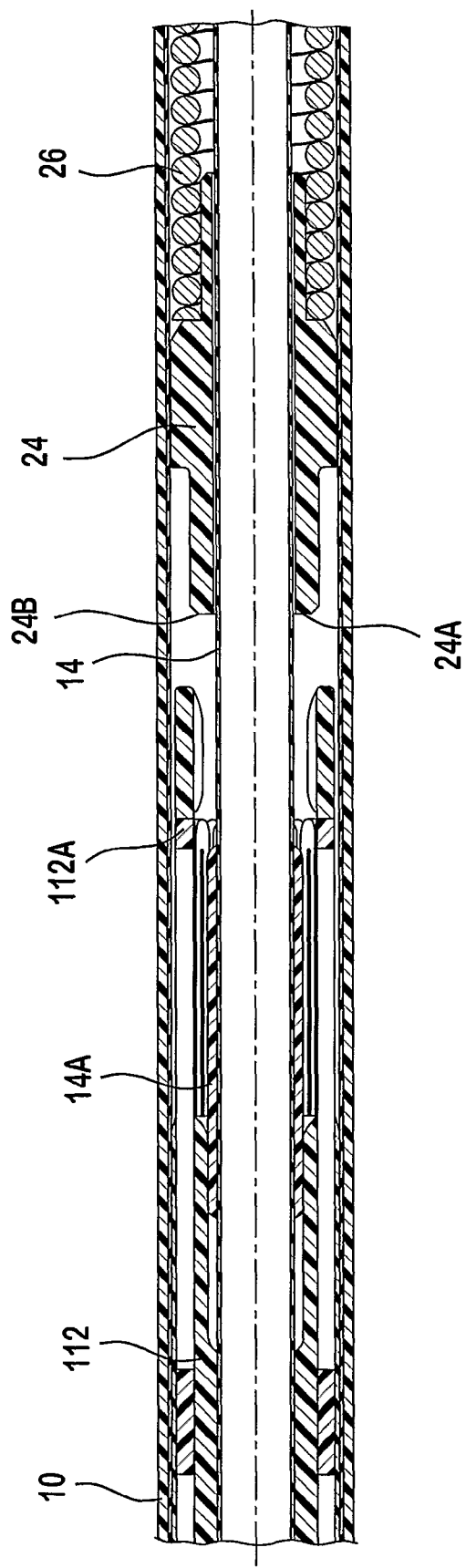
FIG. 4 is an enlarged view of a mid-portion of the device in FIG. 2. The mid-portion includes a proximal end of the stent graft with a pusher element.

Referring to FIG. 4, the stent 112 includes a proximal end 112A disposed so that a portion of the stent 112 is contiguous to a boss 14A of inner shaft 14. A member that provides a pusher 24 is coupled to a coil spring 26. The pusher 24 is configured to provide a through opening 24A so that a portion of the inner shaft 14 passes through the opening 24A. The pusher 24 is coupled to coil spring 26, which is coupled to the outer shaft 15 via a boss portion 15A by a suitable technique such as, for example, bonding, welding, brazing, or press fit via radial coil spring force. By coupling the pusher 24 to the shaft 15, the pusher 24 is allowed to move relative to the inner shaft 14 and the outer sheath 10. The shoulder of 24 is provided for contact with the proximal end portion of the stent 112 as the outer shaft 15 is moved in a proximal direction (from right to left in the drawings).

Figure 5:
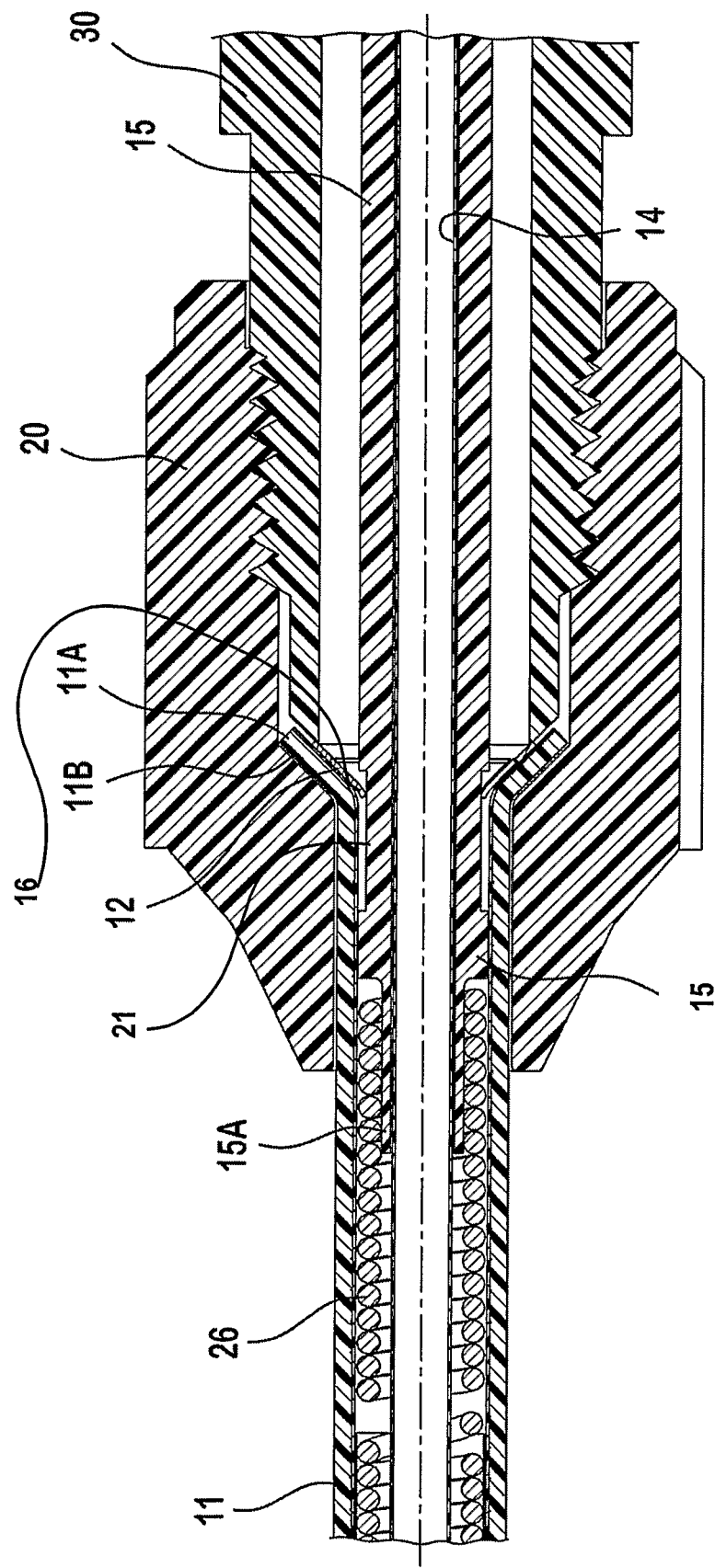
FIG. 5 is an enlarged view of a coupler portion of the device of FIG. 2. The coupler portion includes a swivel nut and a flexible joint.

Referring to FIG. 5, the sheath 10 and a liner 12 are captured to a boss portion or swivel nut 20 via a flared end 11A of the sheath 10. The flared end 11A can be joined to the inside tapered surface A by a suitable joining technique such as, for example, bonding, gluing and welding. In a preferred embodiment, the flared end 11A is joined by gluing the two components together with a suitable adhesive 11B such as, for example, Locktite®. The boss 30 can be used to capture the liner 12 and the sheath 10 between the swivel nut 20 and the flared end 11A.

The inner shaft 14 extends through a sealing boss 32 (FIG. 2), which is threaded on its outside surface for engagement with the threaded portion of the boss 30. The sealing boss 32 itself carries an internal thread which receives an outside thread on a fluid manifold 44. This manifold 44 can be provided with an axial through-bore with an O-ring seal 34, which seals with the outer shaft 15. The fluid manifold 44 has a fluid inlet tube with a valved adapter 42, which allows injection of liquid into the annular space between the sheath 10 and the inner shaft 14, as appropriate, for radiology or for aspiration during a stent graft procedure. The inner shaft 14 is coupled to an outer shaft 15 that extends to the adapter body 80 via connection 70. The preferred configuration of the inner shaft 14 and outer shaft 15 at the adapter body 80 is shown in detail in FIG. 6.

In FIG. 6, the proximal end of the shaft 15 is coupled to the inner shaft 14 and coil member 26. In the preferred embodiment, the inner surface 15A of the outer shaft 15 is bonded to the outer surface 14A of the inner shaft 14. To ensure that the outer shaft 15 and the inner shaft 14 remains fixed relative to each other, a suitable adhesive is provided between a shoulder 15B and the outer surface 14A of the inner shaft 14. Preferably, the outer shaft 15 is a metallic hollow shaft whereas the inner shaft 14 is a polymeric hollow tubing.

To prevent the inner shaft 14 from being pulled proximally through the swivel nut 20 or the manifold 44, a suitable locking mechanism can be provided on the outer surface of the inner shaft 14 or outer shaft so that the inner shaft 14 is prevented from being pulled through the swivel nut 20. Alternatively, a suitable mechanism can be provided on the inner surface of the swivel nut 20 or manifold 44 to prevent over-extension of the inner shaft 14 through the swivel nut or manifold 44. Other appropriate locations can be used to prevent the movement of the inner shaft 14 in the proximal direction (left to right in the drawings). For example, a lock mechanism can be provided in the threaded boss 30 to engage with a corresponding mechanism in the pusher 24 to prevent movement of the shaft 15 proximally (left to right in FIGS. 4-6) through the boss 30 but allow for distal movement (right to left in FIGS. 4-6).

In one preferred embodiment of a locking mechanism, the outer shaft includes a groove that is engaged by a retaining ring 16 disposed about the outer shaft 15 and secured to the assembled swivel nut and boss 30. More specifically, as seen for example in FIG. 5, the distal end of the outer shaft 15 preferably includes a longitudinally extending groove 21 having disposed therein a portion of the retaining ring 16. The retaining ring is preferably an annular member having an outer perimeter and an inner perimeter defining a central bore through which the inner shaft and outer shaft is disposed. The proximal and distal ends of the groove 21 engage the inner perimeter of the ring 16 to limit proximal and distal travel of the inner and outer shaft through the swivel nut 20 and boss 30. The ring 16 is preferably captured between the threaded engagement of the boss 30 and the swivel nut and can further be in contiguous with the flared distal end of the outer sheath 10.

Figure 7A:
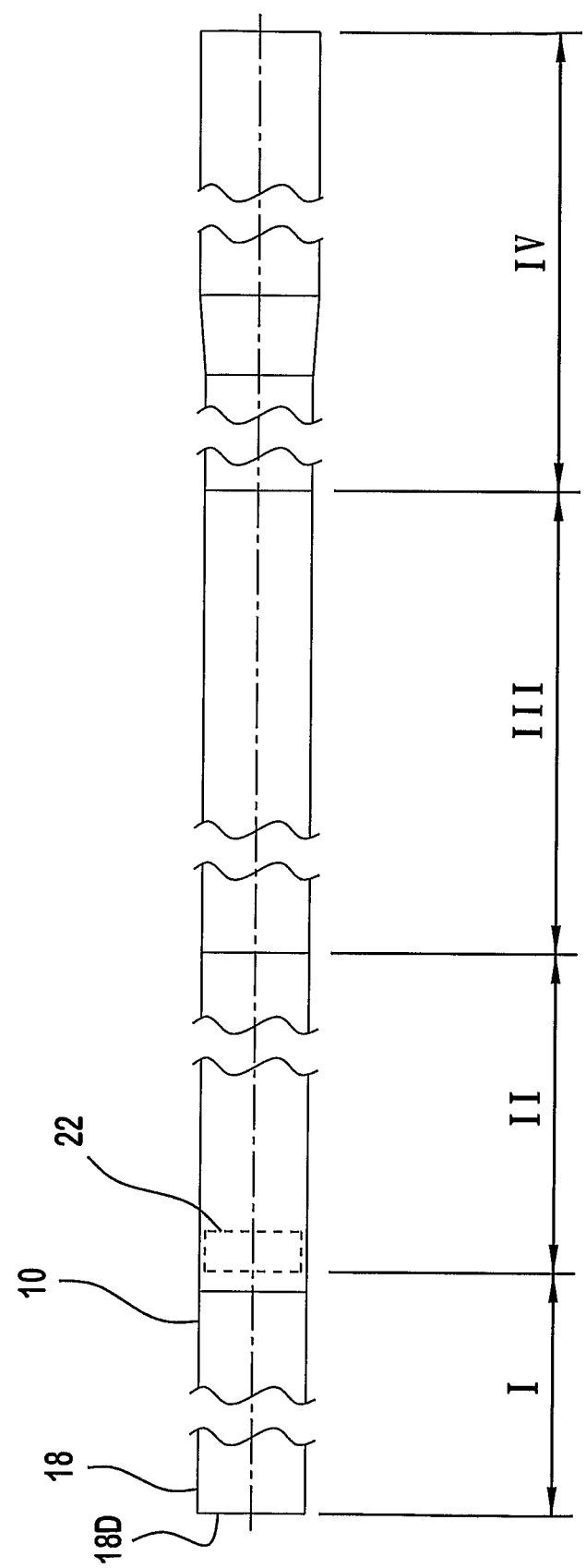
FIG. 7A illustrates the outer sheath 10 in an intermediate manufacturing stage.
Figure 7B:
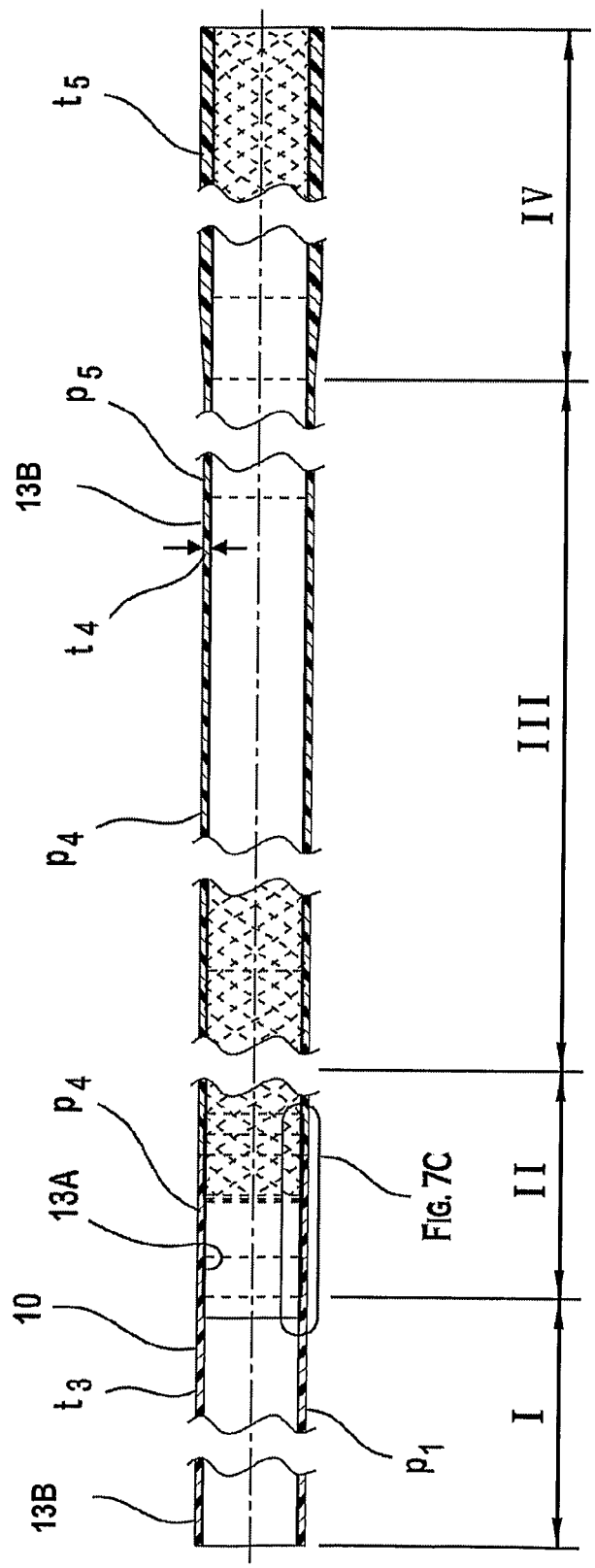
FIGS. 7B and 7C are successive magnification of portions of the outer sheath 10.
Figure 7C:
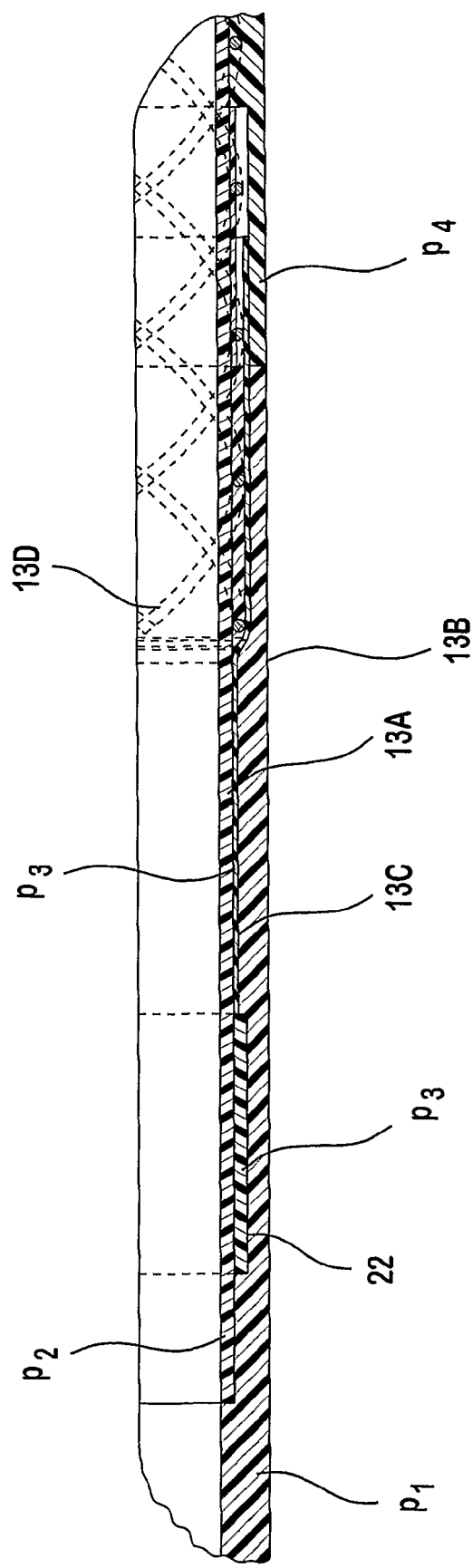

Turning now to FIG. 7A, the sheath 10 is shown as a separately formed member in an intermediate stage of assembly. The sheath 10 is configured from a combination of materials to achieve the advantages of the preferred embodiments. It should be noted that in FIGS. 7A-7C, the outer sheath 10 is in its intermediate stage where the tapered tip 18 portion has not been formed and therefore the tip 18 is generally cylindrical in shape. As shown in FIGS. 7B and 7C, the sheath 10 can be configured to have an inner layer 13A, outer layer 13B, intermediate layer 13C, and a braiding 13D disposed between a portion of the inner and outer layers 13A and 13B.

The outer layer 13B for the sheath 10 is provided in FIGS. 7A and 7B as four separate portions I, II, III, and IV with respective variations in durometer value for each portion. In distal portion I of the sheath 10, the outer layer 13B can be a first polymer such as, for example, a thermoplastic polymer, preferably polyether block amides including those known by trade names of Estamid® or PEBAX® and most preferably PEBAX® 3533 (manufactured by Elf Atochem). In the proximal portion IV, the outer layer 13B of the sheath 10 can be formed from another polymer such as, for example, polyamide Nylon® resin, such as, for example, Nylon 75D, which is reinforced by braiding 13D. In the second portion II, the outer layer 13B can be made from PEBAX® 6333. In the third portion III, the material for the outer layer 13B can be PEBAX® 7233. The discrete outer layer 13B changes from portion I to portion III and is preferably accomplished in three parts from a lower durometer value to a higher durometer value. Preferably, the outer layer 13B is formed with PEBAX® 3533, PEBAX® 6333, and then to PEBAX® 7233, and thereafter to Nylon 75D. The overall length of the outer sheath 10 can be in various lengths such as, for example, 80 or 120 centimeters. The inner layer 13A, which is offset over a distance of about 10 millimeters from the opening 18D of the tip 18, can be formed out of a thermoplastic, most preferably PEBAX® 6333. In one preferred embodiments, the length of section I is about 15 millimeters; length of section II is about 20 millimeters; length of section III is at least 775 millimeters; and the length of section IV is at least 50 millimeters.

The outer sheath 10 can be constructed by at least one manufacturing process to provide for the advantages of the preferred embodiments. In the preferred embodiments, the sheath 10 is formed by placing the inner layer 13A over a mandrel (not shown), which is preferably lined with PEBAX® 6333. A braiding 13D is placed over the inner layer 13A with a portion cut back from the distal end of the layer 13A so that a small portion of polyethylene terephthalate ("PET") is placed over the braiding 13D from the other end. The braiding 13D are located so that they are not exposed to the luminal surface. The PET liner 13C is heated so that it conforms to the braiding 13D and inner layer 13A. Any frayed wire ends of the braiding 13D can be removed by a suitable technique, such as, for example, etching or sand blasting. Also, the braiding end can be covered by the PET liner 13C. The marker 22 can be placed over the assembly until the marker 22 abuts the PET layer 13C. Several sections of the outer liner 13B with different durometers can be placed over the partial manufactured assembly so that each section of the outer layer 13B abuts the other section. A suitable technique can be used to join the various sections together. Preferably, a heat source with heat shrink tubing is used to join the various discrete polymeric portions as the sheath 10. The sheath 10 can be joined to the end tube portion 11 by a suitable joining technique, such as, for example, melding the sheath 10 to the portion 11. In the preferred embodiments, the various sections of outer layer 13B are formed as a plurality of discrete PEBAX® plastics and Nylon plastic joined together to form the device 100.

The sheath 10 is formed by at least three different polymers for its outer layer with respectively increasing durometer values. The sheath 10 is formed by at least three different polymers for its outer layer with respectively increasing durometer values (FIG. 7C). Between the sheath portions I and II, there is preferably provided a first polymer P1 (PEBAX® with a first durometer value) that arcuately or circumferentially surrounds a second polymer P2 (also PEBAX® with a higher durometer value than the first polymer P1) and a third polymer P3 (PET). The third polymer is preferably disposed between the first polymer P1 and the second polymer P2. The third polymer P3 (polyethylene or "PET") is utilized to couple the braiding 13D to the first and second polymers. The braiding 13 preferably utilizes metallic wire (e.g., stainless steel) having a preferable diameter of about 0.05 mm at a density of 45 crossings per linear inch of the shaft length (17.5 crossings per linear centimeter of the shaft length). One end of the third polymer P3 abuts against the marker 22 to prevent its movement during assembly. The other end of the third polymer P3 is preferably surrounded by a heat melted polymer to prevent blooming of the polymer or the braiding. A distal end of the second polymer P2 is joined to the first polymer P1 at a shoulder, preferably by heat melting one of the polymers together or both together. The distal end of the third polymer P3 ("PET") is preferably about 0.5 millimeters apart from the nearest portion of marker 22. The marker 22 is preferably about 1 millimeter in length. The marker 22 can be located about 1.5 millimeters from a terminal end of the braiding 13D. The second polymer P2 extends along the axis X over a distance of greater than 10 millimeters and is joined to a fourth polymer P4 so that both polymers extend over a distance of at least 80 millimeters. Preferably, the fourth polymer has a higher durometer value than the first polymer P1 or the third polymer P3. The fourth polymer P4 is joined to a fifth polymer P5, which is preferably Nylon 75D. Both the fifth polymer P5 and the second polymer P2 extend over a distance of at least 20 millimeters. And as used herein, the term "durometer" indicates a quantification of the resistance of plastics toward indentation and provides an empirical hardness value. One example of the known quantification is Shore Hardness, using either the Shore A or Shore D scale. The ASTM test number for durometer testing is believed to be ASTM D while the analogous ISO test method is believed to be ISO 88.

The tapered tip can be formed in the manner generally described in U.S. Patent Application Publication No. 2002-0183826 A1 published on Dec. 5, 2002, which Publication is incorporated by reference herein in its entirety. In particular, a mandrel is provided with a section for forming the tip 18 that includes a cylindrical distal tip-section. The distal section of the outer sheath 10 is necked down to create a pre-form shaped like a bottleneck. Preferably, the braiding and the PEBAX® layer of the outer catheter 10 extend distally to the proximal end of the necked down section whereof the tip is being formed. For the tip-shaping operation of the pre-form, the mandrel is advanced from the proximal to the distal end of the outer catheter 10 until a cylindrical section projects distally out of the pre-form. Then, the mandrel, together with the pre-form, is inserted into a hollow mold. The mandrel is first centered by inserting the cylindrical tip-section into a corresponding bore of the hollow mold, which has a snug fit. Then the distal end of the pre-form is advanced until it touches the inner wall of the hollow mold. For forming the final tip shape in the mold cavity, the mold is heated, to thermoform the tip shape in the cavity between the mold and the mandrel. During this heating phase the mandrel is pressed into the hollow mold to form the final tip. The form closure between the cylinder of the mandrel and the respective opening prevents the leaking of material out of the molding section. The forming during the heating phase is followed by a cooling phase before the mandrel is withdrawn proximally and the formed tip is taken out of the hollow mold.

Alternatively, the cylindrical section of sheath 10 is inserted into an outer mold and an inner mold is inserted through the hollow volume defined by the sheath 10. Heat is applied in order to force the thermoplastic cylindrical section I to conform to the inner and outer molds. The inner mold can be withdrawn in a proximal direction or in a distal direction through the now formed taper tip 18. Due to the decrease in wall thickness of the tapered tip 18, the inner mold can be preferably withdrawn distally through the tapered tip portion 18 so as to form the distal opening 18.

There are several design parameters that are believed to be heretofore not available in the state of the art. First, the entrant port 19 to the inner shaft 14 is provided with a flared (tulip-like) opening 19A, which is substantially larger than the outer diameter of a guide wire. The tulip opening 19A ensures that insertion of the guide wire will not result in the tip 18 of the guide wire being inserted into a dead space 19D between the inner surface 18B of the outer sheath 10 and the outer surface of the tulip 19A.

Second, the inner shaft 14 of the preferred embodiments is not connected to an external tip 18. In other words, the preferred embodiment is distinct from the known delivery device that includes an atraumatic tip (e.g., rounded cone) for the outer catheter. Furthermore, the inner shaft 14 is provided as part of a delivery device that includes the third feature of the outer sheath 10, as described above.

Third, the inner shaft 14 of the preferred embodiments is provided with a stop mechanism to prevent retraction of the inner shaft 14 and outer shaft 15 through the swivel nut 20 or the manifold 44 and out through the manifold 44.

Fourth, the tapered atraumatic tip 18 provides an increasing thickness from the opening of about 0.1 millimeter to the base of the taper of about 0.2 millimeter. The increase in thickness from the opening 18D to the base 18C of the tip 18 is believed to exert pressure on the stent graft 112 so as to prevent a premature release of the stent graft 112. It is also believed that the tapering thickness allows for a lower deployment force of the stent graft 112.

Figure 8A:
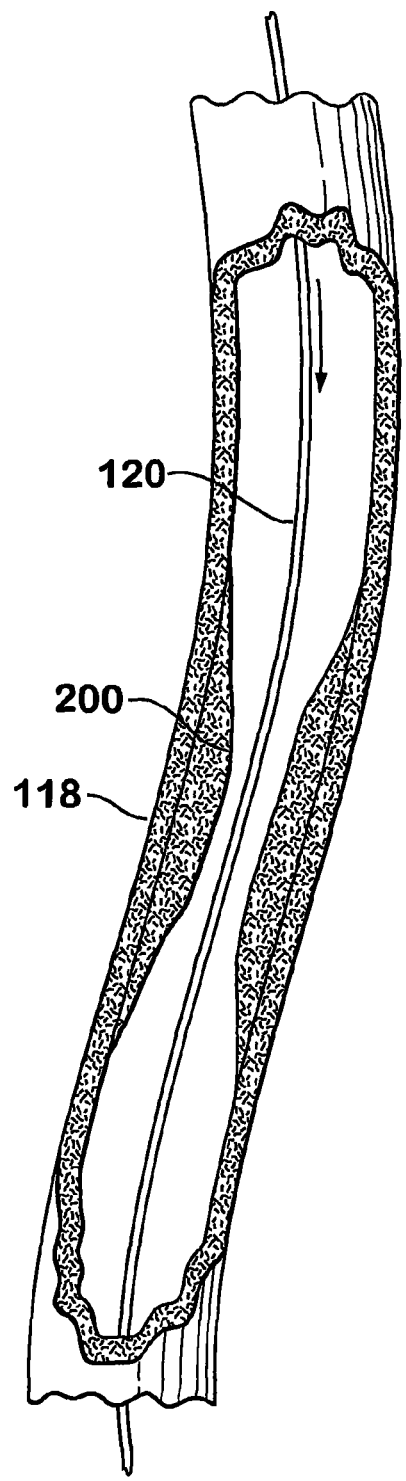
FIGS. 8A-8I illustrate a simulated deployment of a stent graft proximate a simulated stenosis area in a body vessel.
Figure 8B:
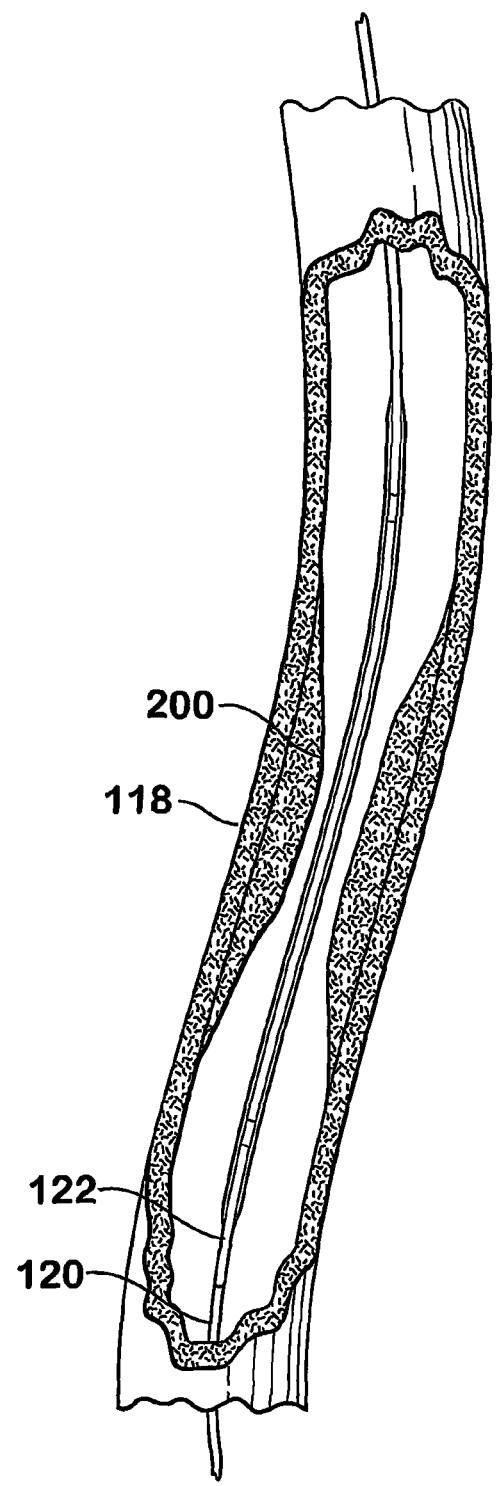
Figure 8C:
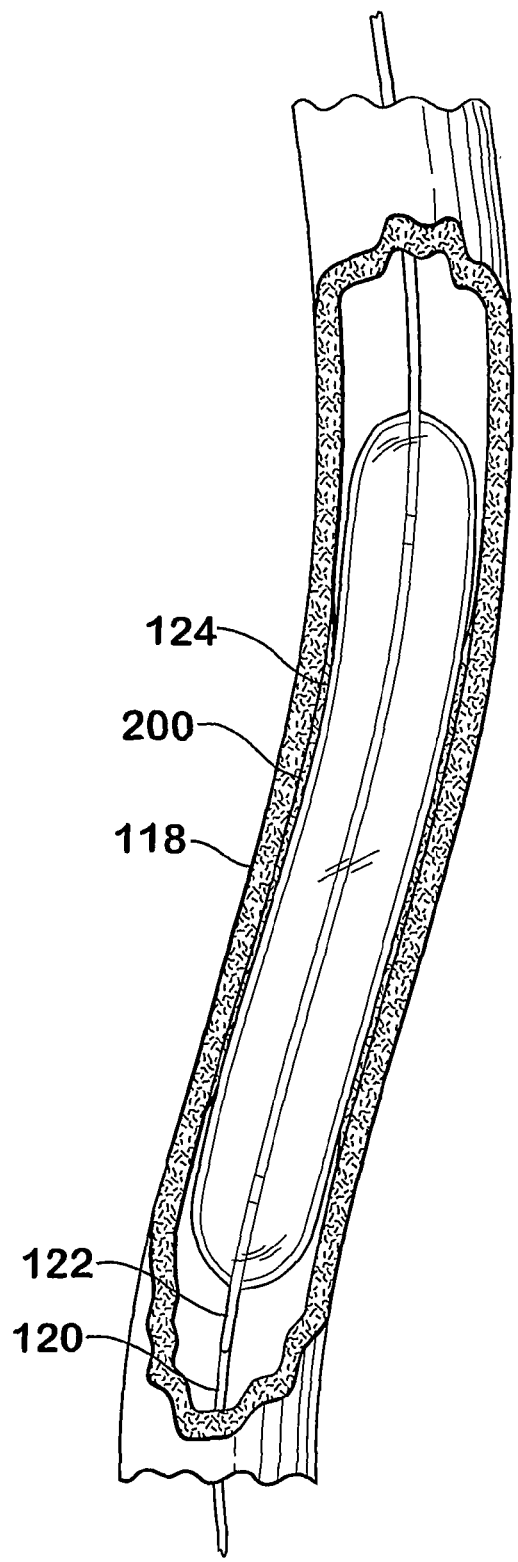
Figure 8D:
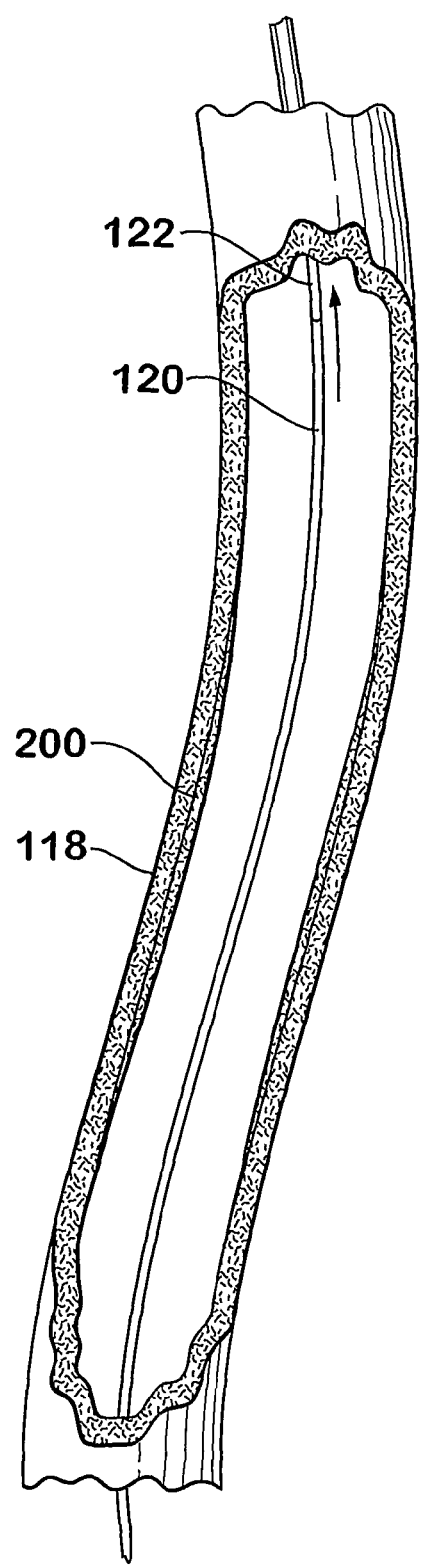
Figure 8E:
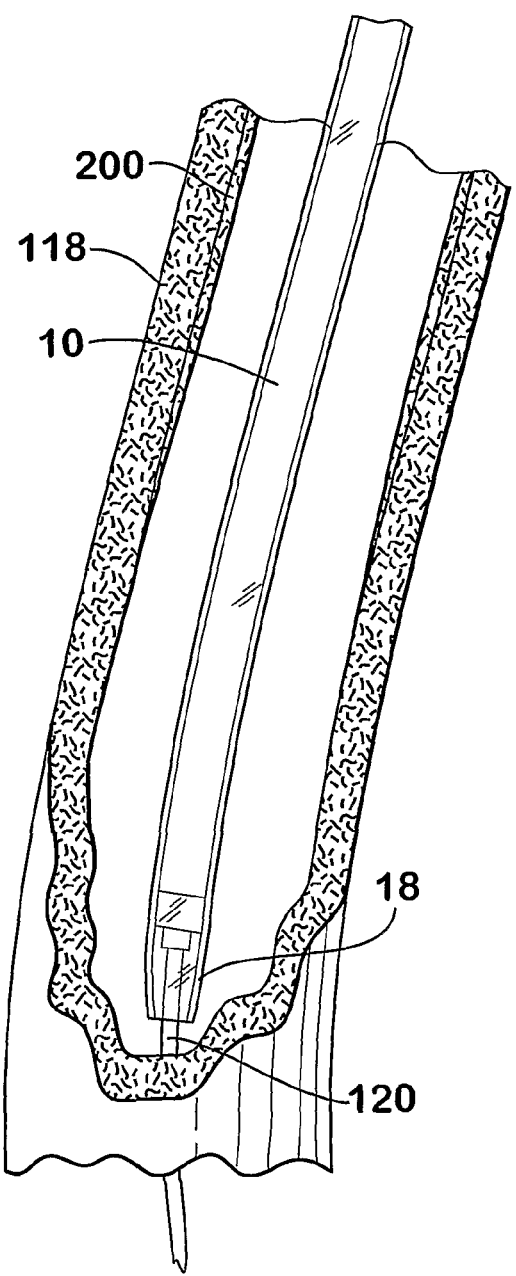
Figure 8F:
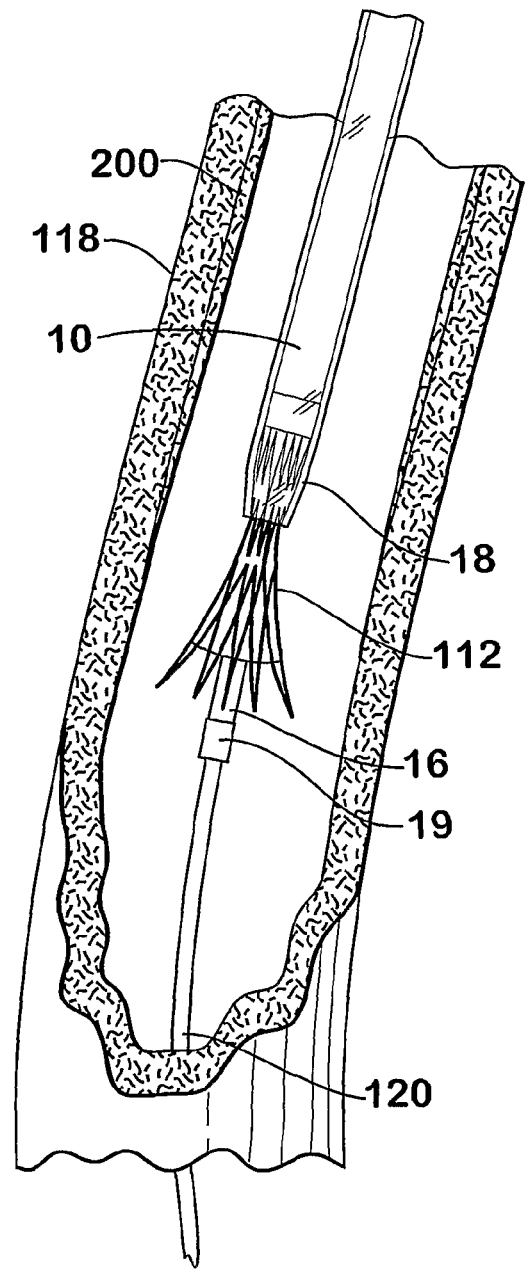
Figure 8G:
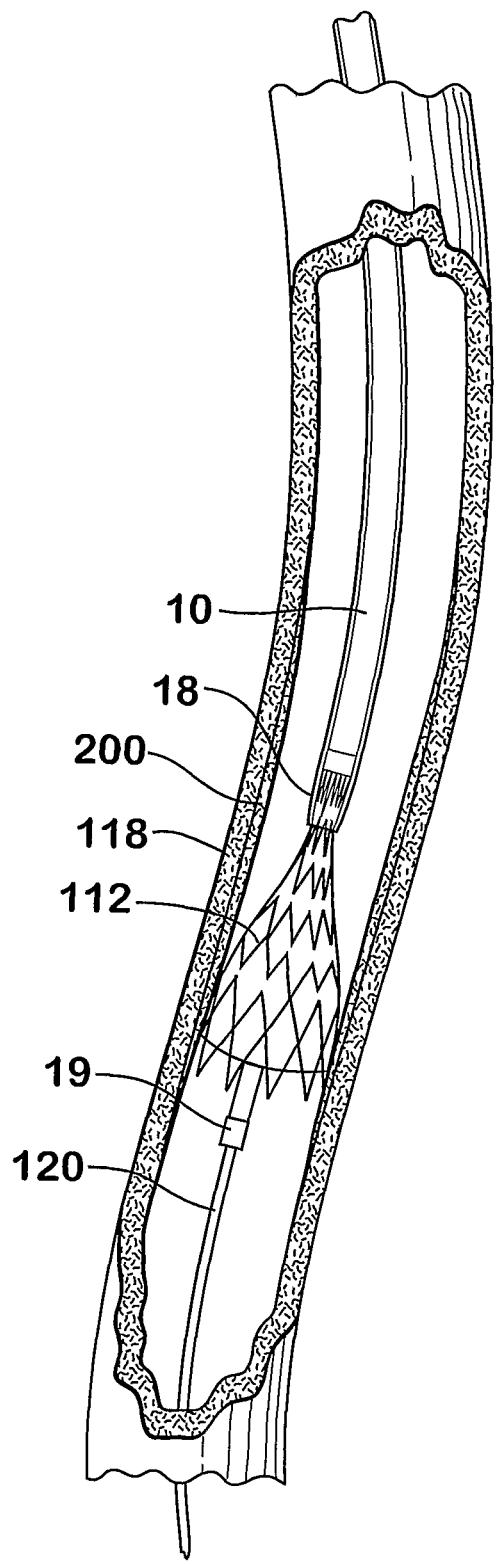
Figure 8H:
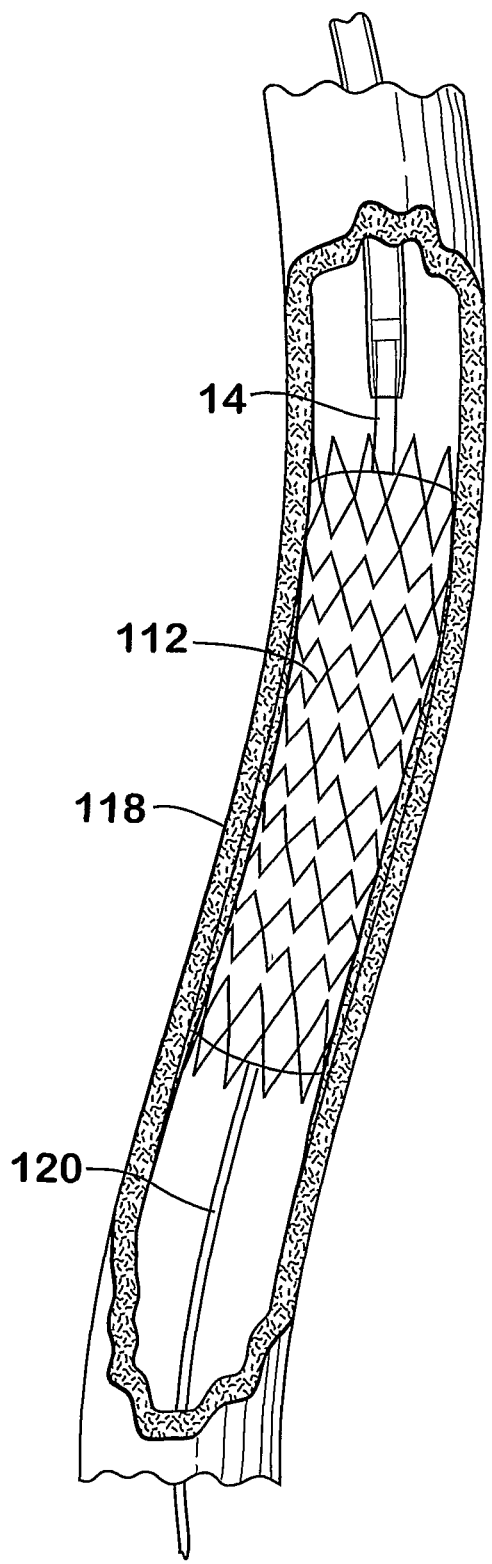
Figure 8I:
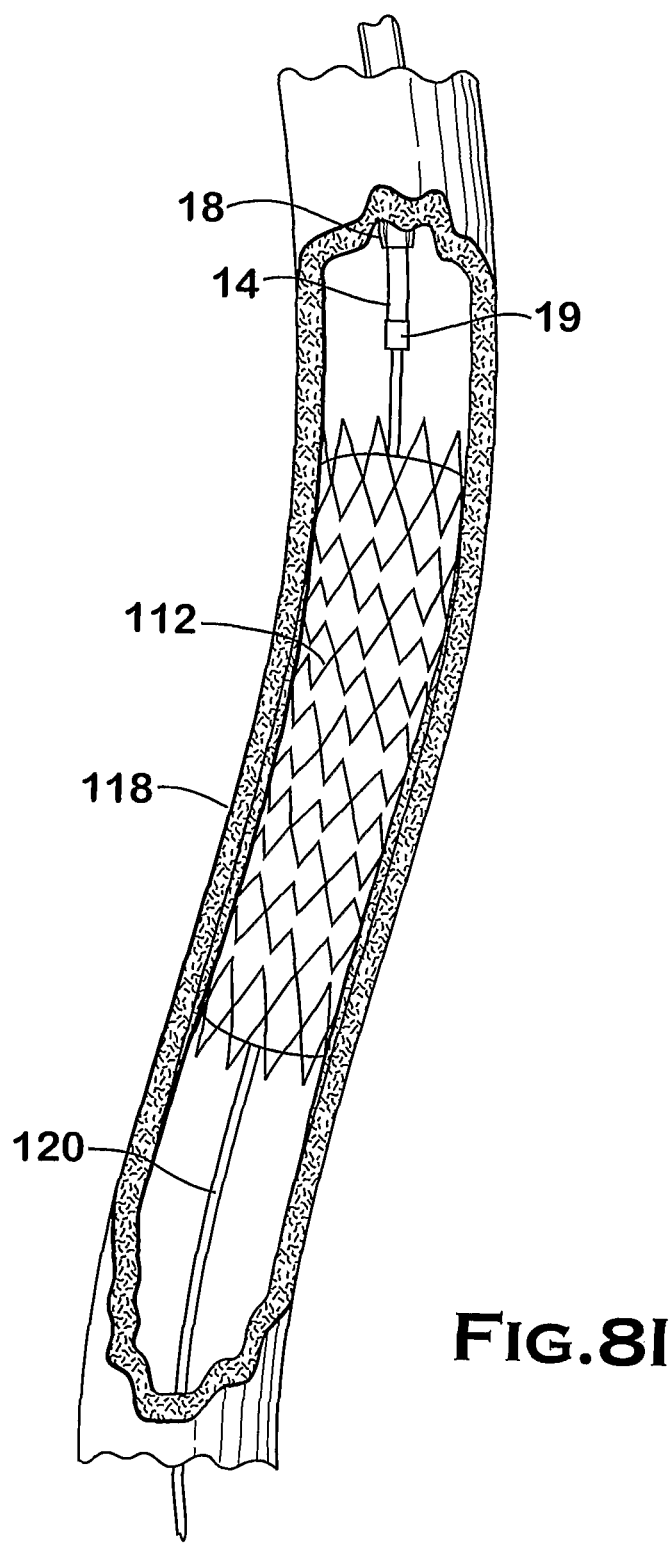
Figure 9:
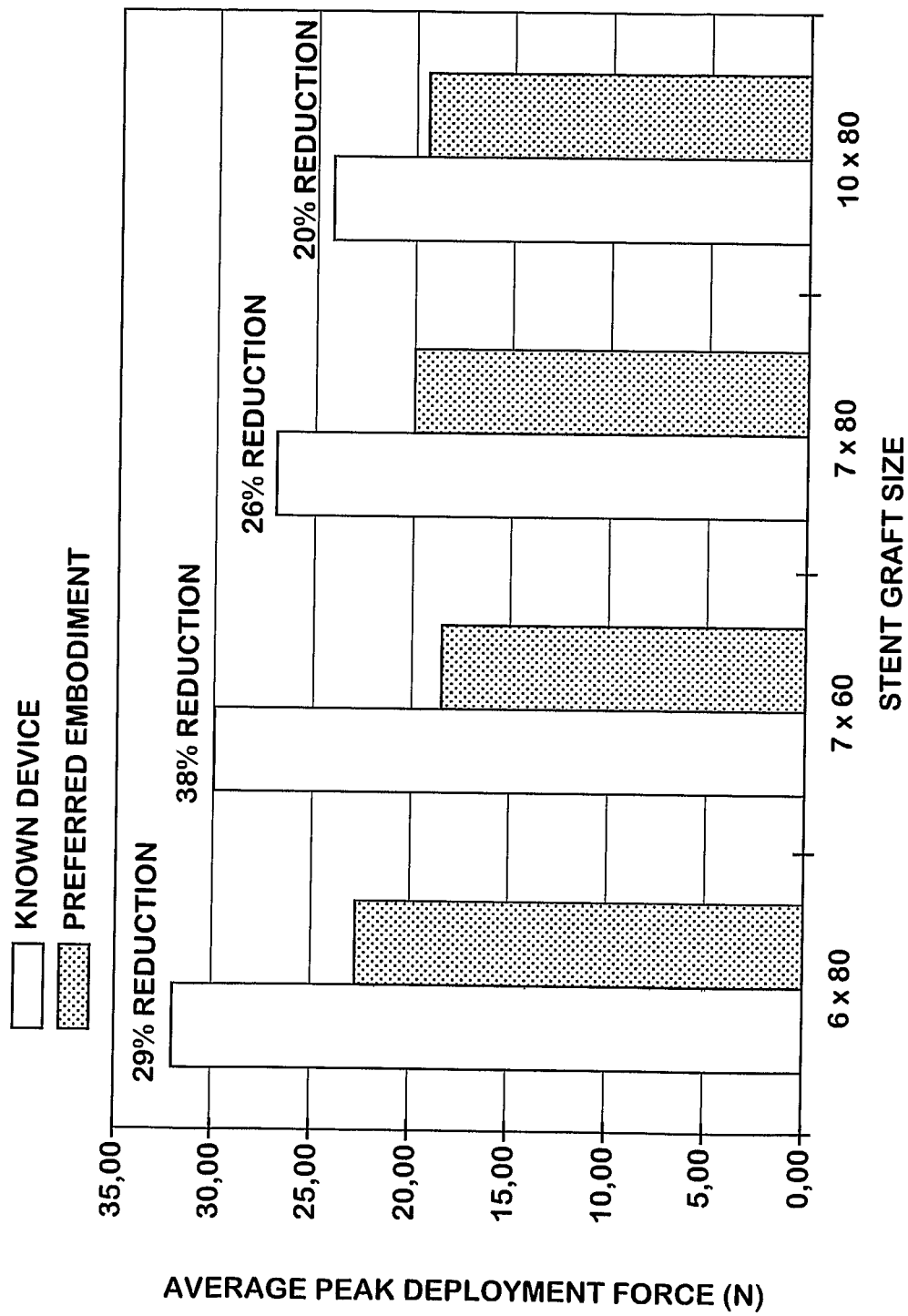
FIG. 9 is a graphical comparison of deployment forces for various stent graft sizes for a known delivery device and the delivery device of FIG. 1.

To better demonstrate some of the benefits of the preferred embodiments, a simulated deployment of a stent graft 112 in a body vessel is illustrated in FIGS. 8A-8I. In FIG. 8A, a simulated vessel 118 is shown with a stenosed region 200 and a guide wire 120 passing through the stenosed region 200. A balloon catheter 122 can optionally be utilized to increase the flow area through the stenosis prior to implantation of the stent graft 112, as shown in FIGS. 8B and 8C. Thereafter, the balloon 122 is retracted along the guide wire 120.

In one preferred method of use of the delivery device 100, the device 100 and stent graft 112 are prepared for deployment. More specifically, with the stent graft 112 secured about the inner shaft 14 in an undeployed state by the sheath 100, the lumen of the stent graft 112 can be flushed with a sterile saline. First the Tuohy-Borhst valve 50 is secured about the Y-adapter 40. A syringe of sterile saline solution can be coupled to the Y-adapter, and upon ensuring that the fluid valve 42 is open, the saline can be injected to flush the lumen of the stent graft 112. Saline is preferably continuously injected until drops of the solution is observed discharging from the tip 18 of the outer sheath 10. The lumen of the inner shaft 14 can also be prepared with a saline flush by coupling another syringe of saline to the luer-adapter 90.

With the stent graft 112 ready for deployment, the device 100 is engaged with the guide wire 120 and the outer sheath 10 is advanced, preferably under radiographic guidance, so as to locate the tapered tip 18 to a point distal of the stenosis as illustrated in FIG. 8E. Using the radiopaque markers of the stent graft 112 as visual cues, the stent graft 112 can be centered across the stenosis. Any fine adjustment that is needed to center the stent graft 112 across the stenosis is preferably performed by drawing the device 100 backward along the guide wire. Where the deployment is being observed on a visual monitor, the radiopaque markers on the stent graft ends can be used to verify that the stent graft 112 is straight and centered across the stenosis. Preferably, the proximal and distal ends of the stent graft 112 is marked on the monitor for reference. The radiopaque markers can also be used to visually verify and adjust the device 100 to ensure that the device 100 is straight.

With the stent graft 112 centered about the stenosis, the Tuohy-Borst valve can be opened and the safety device 60 is preferably removed by pulling the device 60 downward. The sheath 10 can then be retracted in the proximal direction towards the operator (e.g., the physician) of the delivery device, as shown in FIG. 8F, by applying a deployment force and pulling the Y-adapter 40 toward the adapter body or handgrip 80. This action by the operator causes the tip 18 to expand flexibly (i.e., flaring) outward over the tulip entrant port 19 and over the stent graft 112 to expose the stent graft 112. Preferably, about fifteen millimeters of the distal end of the stent graft 112 is exposed and allowed to anchor before deploying the remainder of the stent graft 112. The location of the stent graft can be preferably continuously verified by checking the location of the makers on the stent graft 112 against the reference markers on the monitor. The device 100 is preferably maintained as straight as possible. Accordingly, a back tension is preferably continuously applied to the handgrip 80. In addition, the handgrip is preferably continuously maintained in a constant location with only the Y-adapter being drawn proximally.

As the sheath 10 is continually retracted proximally (i.e., towards the operator of the delivery device 100), the stent graft 112 is fully deployed, shown here in FIG. 8H. In the preferred embodiment of the device 100, full deployment of the stent graft can be indicated by contact between the Y-adapter and the handgrip 80. In addition, where the proximal end of the stent graft 112 includes a plurality of marker, the markers will visually appear separated upon full deployment. After the stent graft 112 is fully deployed, the tulip-like entrant port 19 of the inner shaft 14 is retracted proximally towards the operator of the delivery device 100, shown here in FIG. 8I. Optionally, a balloon catheter can be utilized to further expand the stent-graft 122 in the vessel 118.

The average deployment force for stent grafts 112 (commercially available under the trade name "Fluency" from Bard Peripheral Vascular Inc., ("BPV")) as described, shown, and claimed in U.S. Pat. Nos. 5,707,386; 5,716,393; 5,827,327; 5,860,999; 6,053,941; 6,124,523; 6,383,214; 6,436,214; and 6,436,135, which are incorporated herein by reference in their entirety) in sizes 6 mm by 80 mm (BPV Part No. FLT06080), 7 mm by 60 mm (BPV Part No. FLT07060), 7 mm by 80 mm (BPV Part No. FLT07080), and 10 mm by 80 mm (BPV Part No. FLT10080) is less than 33 Newton force with at least a 20% reduction in force as compared to the known delivery device. For example, as used with a stent graft 112 with a diameter of 6 mm by 80 mm, the average deployment force is about 23N; for a stent graft 112 with a diameter of 7 mm by 60 mm, the average deployment force is less than 17N; for a stent graft 112 with a diameter of 7 mm by 80 mm, the average deployment force is less than 30N and preferably 17N; for a stent graft 112 with a diameter of 10 mm by 80 mm in length, the average deployment force is less than 20N.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An implant delivery device comprising:
a first shaft having a proximal portion and a distal portion, the first shaft having an outer surface and an inner surface defining a first lumen along a longitudinal axis, the distal portion having a tip defining a taper in the distal direction toward the longitudinal axis and terminating at a distal opening;

a second shaft having a proximal portion and a distal portion and an inner surface defining a second lumen therebetween having a first cross-section, the second shaft disposed within the first lumen such that the second lumen is generally coaxial with the first lumen to define a chamber, the distal portion of the second shaft terminating in a port having an opening in communication with the distal opening of the first shaft, the opening of the port having a second cross-section greater than the first cross-section.

2. The implant delivery device of claim 1, wherein the port includes a flared portion extending in a distal direction toward the inner surface of the first shaft.

3. The implant delivery device of claim 2, wherein the port includes a portion distal of the flared portion that is parallel to the longitudinal axis.

4. The implant delivery device of claim 2, wherein the distal portion circumscribes the longitudinal axis such that at least a portion of the port is substantially frusto-conical.

5. The implant delivery device of claim 2, wherein the flared portion circumscribes the longitudinal axis such that at least a portion of the port is substantially tulip-shaped.

6. The implant delivery device of claim 1, further comprising an inner shaft having a proximal portion, a distal portion, an outer surface and an inner surface defining a lumen, the inner shaft disposed in the lumen of the second shaft such that distal portion of the second shaft directs a guide wire from the distal opening of the first shaft to the lumen of the inner shaft.

7. The implant delivery device of claim 6, wherein the outer surface of the inner shaft is substantially contiguous with the inner surface of the second shaft along a substantial length of the second shaft.

8. The implant delivery device of claim 6, wherein the second shaft is coupled to the inner shaft such that the second shaft is slidable along the longitudinal axis relative to the first shaft.

9. The implant delivery device of claim 6, wherein the proximal portion of the second shaft terminates along a portion of the inner shaft between the distal and proximal portion of the inner shaft.

10. The implant delivery device of claim 6, wherein the outer surface of the inner shaft defines a maximum distance transverse to the longitudinal axis and the inner surface of the second shaft defines a maximum distance transverse to the longitudinal axis, the maximum transverse distance of the second shaft being about ten percent greater than the maximum transverse distance of the inner shaft.

11. The implant delivery device of claim 1, wherein the outer surface and the inner surface of the tip define a wall.

12. The implant delivery device of claim 11, wherein the wall has a thickness that decreases in a direction along the longitudinal axis from the proximal portion to the distal opening.

13. The implant delivery device of claim 12, wherein the wall thickness decreases from a maximum of about 0.2 millimeters to a minimum of about 0.1 millimeters.

14. The implant delivery device of claim 13, wherein the thickness decreases at a substantially constant rate over the axial length of the tip.

15. The implant delivery device of claim 1, wherein the taper of the tip defines an acute angle with a line parallel to the longitudinal axis, the angle ranging from about eight degrees to about twenty degrees.

16. The implant delivery device of claim 1, wherein the distal portion of the first shaft includes at least one radiopaque marker for identifying the position of an implant in the chamber.

17. The implant delivery device of claim 16, wherein the at least one marker comprises an annular member secured to the first shaft having about ninety percent platinum and about ten percent iridium.

18. The implant delivery device of claim 1, wherein the outer and inner surface of the first shaft proximal the tip define a wall thickness that increases in a direction from the distal portion to the proximal portion, ranging from about 0.2 millimeters to about 0.3 millimeters.

19. The implant delivery device of claim 1, wherein the tip is substantially made of PEBAX® having a durometer of about 40D.

20. The implant delivery device of claim 1, wherein the first shaft has at least two slits, the at least two slits extending axially along the length of the tip diametrically opposite one another about the distal opening.

21. The implant delivery device of claim 1, wherein the port includes an aperture to provide communication between the tip and the lumen of the second shaft.

22. An implant delivery device comprising:
an inner shaft having a first diameter extending between a proximal end and a distal end spaced apart along a longitudinal axis, the inner shaft terminating in a port having a second diameter greater than the first diameter; and
an outer sheath disposed about the inner shaft, the outer sheath terminating in a distal tip tapering toward the longitudinal axis, the outer sheath being movable along the longitudinal axis in a proximal direction relative to the inner shaft to expose the port, the outer sheath having a layer including a proximal portion, a distal portion, and at least one intermediate portion therebetween, the proximal, distal and at least one intermediate portions being discrete portions along the longitudinal axis, each having a discrete durometer.

23. The implant delivery device of claim 22, wherein the distal portion comprises a thermoplastic polymer, the proximal portion comprises polyamide Nylon and the at least one intermediate portion being one of PEBAX® 6333 and PEBAX® 7233.

24. The implant delivery device of claim 22, wherein the durometers of the discrete portions increase from the distal portion to the proximal portion.

25. An implant delivery device comprising:
an inner shaft having a proximal end and a distal end spaced apart along a longitudinal axis; and
an outer sheath having a proximal portion, a distal portion and at least one intermediate portion therebetween, the outer sheath being disposed about the inner shaft, the outer sheath being movable along the longitudinal axis relative to the inner shaft; the outer sheath having an outer layer of a first polymer, an inner layer of a second polymer having a durometer greater than that of the first polymer, an intermediate layer of at least a third polymer disposed between the first and second polymer, and a braiding disposed between a portion of the inner and outer layer, the intermediate layer joining the braid to the first and second polymer.

26. The implant delivery device of claim 25, wherein the first and second polymer are PEBAX® and the third polymer comprises PET.

27. The implant delivery device of claim 25, wherein the first polymer is disposed between the distal portion and the at least one intermediate portion.

28. The implant delivery device of claim 25, wherein the first polymer includes at least one shoulder, the second polymer engaging the shoulder to join the first polymer to the second polymer.

29. The implant delivery device of claim 25, wherein the braiding comprises a metallic wire having a diameter of about 0.05 millimeters at a density of 45 crossings per linear inch.

30. The implant delivery device of claim 25, wherein at least a portion of the third polymer is surrounded by a heat melted polymer.

31. The implant delivery device of claim 25, further comprising at least one marker disposed about 1.5 millimeters from a terminal end of the braiding so that the marker abuts the third polymer.

32. The implant delivery device of claim 31, wherein the marker is about one millimeter in length.

33. The implant delivery device of claim 25, wherein the outer layer of the outer sheath includes a fourth polymer coupled to the second polymer, and a fifth polymer joined to the fourth polymer, the fifth polymer being Nylon 75D.

34. The implant delivery device of claim 33, wherein the second polymer has an axial length greater than ten millimeters, the second and fourth polymers extending in the axial direction over a length of at least eighty millimeters.

35. The implant delivery device of claim 33, wherein the second and fifth polymers extending in the axial direction over a length of at least twenty millimeters.

36. The implant delivery device of claim 33, wherein the fourth polymer has a higher durometer than either of the first or third polymers.

37. The implant delivery device of claim 25, wherein the outer layer of the outer sheath includes a proximal portion, a distal portion, and at least one intermediate portion extending therebetween, the distal portion being a thermoplastic polymer, the proximal portion being a polyamide Nylon, and the intermediate portion being one of PEBAX® 6333 and PEBAX® 7233.

38. The implant delivery device of claim 37, wherein the proximal, distal and at least one intermediate portions of the outer layer of the outer sheath are discrete portions each having a discrete durometer.

39. A catheter sheath comprising:
a first polymer material that circumscribes and extends along a longitudinal axis over a first length; a second polymer contiguous to the first polymer that extends along the longitudinal axis along a second length less than the first and having a surface exposed to the longitudinal axis;
a third polymer interposed between the first and second polymer that extends along the longitudinal axis along a third length less than the first length; and
a marker contiguous to one of the first and second polymers.

40. The catheter sheath of claim 39, wherein the marker comprises a marker disposed between the first and second polymers.

41. The catheter of claim 40, wherein the marker comprises a radiopaque material contiguous to the first, second and third polymers.

42. The catheter sheath of claim 39, further comprising a braiding disposed between the second and third polymer.

43. The catheter sheath of claim 42, wherein the braiding comprises metal wires braided in a cylindrical shape.

44. A catheter sheath comprising:
a proximal portion, a distal portion and at least one intermediate portion therebetween, the sheath having an outer layer of a first polymer circumferentially surrounding an inner layer of a second polymer having a durometer greater that of the first polymer and an intermediate layer of at least a third polymer disposed between the first and second polymer.

45. The sheath of claim 44, wherein the first and second polymer are PEBAX® and the third polymer comprises PET.

46. The sheath of claim 44, wherein the first polymer is disposed between the distal portion and the at least one intermediate portion.

47. The sheath of claim 44, wherein the first polymer includes at least one shoulder, the second polymer engaging the shoulder to join the first polymer to the second polymer.

48. The sheath of claim 44, further comprising a braiding disposed between the inner layer and the outer layer, wherein the braiding is made of a metallic wire having a diameter of about 0.05 millimeters at a density of 45 crossings per linear inch.

49. The sheath of claim 48, wherein the third polymer joins the braiding to the first and second polymers.

50. The sheath of claim 48, further comprising at least one marker disposed about 1.5 millimeters from a terminal end of the braiding so that the marker abuts the third polymer.

51. The sheath of claim 50, wherein the marker is about one millimeter in length.

52. The sheath of claim 44, wherein at least a portion of the third polymer is surrounded by a heat melted polymer.

53. The sheath of claim 44, wherein the outer layer of the outer sheath includes a fourth polymer coupled to the second polymer, and a fifth polymer joined to the fourth polymer, the fifth polymer being Nylon 75D.

54. The sheath of claim 53, wherein the second polymer has an axial length greater than ten millimeters, the second and fourth polymers extend in the axial direction over a length of at least eighty millimeters.

55. The sheath of claim 53, wherein the second and fifth polymers extend in the axial direction over a length of at least twenty millimeters.

56. The sheath of claim 53, wherein the fourth polymer has a higher durometer than either of the first or third polymers.

57. The sheath of claim 44, wherein the outer layer of the outer sheath includes a proximal portion, a distal portion, and at least one intermediate portion extending in between, the distal portion being made of a thermoplastic polymer, the proximal portion polyamide Nylon, the intermediate portion being one of PEBAX® 6333 and PEBAX® 7233.

58. The sheath of claim 57, wherein the proximal, distal and at least one intermediate portions of the outer layer of the outer sheath are discrete portions each having a discrete durometer.

* * * * *